US009328160B2

(12) United States Patent
Ishii et al.

(10) Patent No.: US 9,328,160 B2
(45) Date of Patent: May 3, 2016

(54) ANTI-CDH3 ANTIBODY HAVING HIGH INTERNALIZATION CAPACITY

(75) Inventors: Keisuke Ishii, Tokyo (JP); Keiko Katsumi, Chiba (JP); Tadashi Matsuura, Ibaraki (JP); Yukio Sudo, Tokyo (JP); Katsuyuki Mitomo, Tokyo (JP); Katsushi Kouda, Tokyo (JP)

(73) Assignee: PERSEUS PROTEOMICS INC., Tokyo (JP)

( * ) Notice: Subject to any disclaimer, the term of this patent is extended or adjusted under 35 U.S.C. 154(b) by 39 days.

(21) Appl. No.: 13/882,453

(22) PCT Filed: Oct. 28, 2011

(86) PCT No.: PCT/JP2011/074958
§ 371 (c)(1),
(2), (4) Date: Jul. 19, 2013

(87) PCT Pub. No.: WO2012/057328
PCT Pub. Date: May 3, 2012

(65) Prior Publication Data
US 2013/0317201 A1 Nov. 28, 2013

(30) Foreign Application Priority Data

Oct. 29, 2010 (JP) ................................. 2010-243708
Jul. 7, 2011 (JP) ................................. 2011-150812

(51) Int. Cl.
| | |
|---|---|
| *C07K 16/28* | (2006.01) |
| *C12N 15/13* | (2006.01) |
| *C07K 16/00* | (2006.01) |
| *C07K 16/18* | (2006.01) |
| *A61K 47/48* | (2006.01) |
| *A61K 39/00* | (2006.01) |

(52) U.S. Cl.
CPC ........... *C07K 16/18* (2013.01); *A61K 47/48561* (2013.01); *C07K 16/2896* (2013.01); *A61K 2039/505* (2013.01); *C07K 2317/77* (2013.01)

(58) Field of Classification Search
None
See application file for complete search history.

(56) References Cited

U.S. PATENT DOCUMENTS

| | | | |
|---|---|---|---|
| 8,455,249 B2 * | 6/2013 | Aburatani et al. ............. | 435/344 |
| 2006/0039915 A1 * | 2/2006 | Reinhard ................ | C07K 16/28 424/155.1 |
| 2006/0127407 A1 * | 6/2006 | Chen et al. ................ | 424/178.1 |
| 2013/0245232 A1 * | 9/2013 | Aburatani et al. ......... | 530/387.3 |

FOREIGN PATENT DOCUMENTS

| | | |
|---|---|---|
| EP | 2 426 149 A1 | 3/2012 |
| WO | WO 02/087395 A2 | 12/2002 |
| WO | WO 03/000928 A2 | 1/2003 |
| WO | WO 2006/022344 A1 | 3/2006 |
| WO | WO 2006/114704 A2 | 11/2006 |
| WO | WO 2007/102525 A1 | 9/2007 |
| WO | WO 2008/146854 A1 | 12/2008 |
| WO | WO 2010/001585 A1 | 1/2010 |
| WO | WO 2010/126137 A1 | 11/2010 |
| WO | WO 2011/080796 A1 | 7/2011 |

OTHER PUBLICATIONS

Tsuiji et al. Cadherin conformations associated with dimerization and adhesion. J Biol Chem. Apr. 27, 2007; 282 (17): 12871-82.*
BD Transduction Laboratories. Purified Mouse Anti-P-Cadherin, BD-610227. pp. 1-2, Jan. 13, 2015.*
Holsinger et al. The transmembrane receptor protein tyrosine phosphatase DEP1 interacts with p120(ctn). Oncogene. Oct. 10, 2002;21(46):7067-76.*
de Goeij et al. HER2 monoclonal antibodies that do not interfere with receptor heterodimerization-mediated signaling induce effective internalization and represent valuable components for rational antibody-drug conjugate designmAbs 6:2, 392-402, 2014.*
Rudnick et al. Influence of Affinity and Antigen Internalization on the Uptake and Penetration of Anti-HER2 Antibodies in Solid Tumors. (Cancer Res; 71(6); 2250-9., 2011).*
Akinao Nose et al.; Localization of Specificity Determining Sites in Cadherin Cell Adhesion Molecules; Cell; vol. 61; Apr. 6, 1990; pp. 147-155.
Chikako Yoshida et al.; Teratocarcinoma Cell Adhesion: Identification of a Cell-Surface Protein Involved in Calcium-Dependemetn Cell Aggregation; Cell; vol. 28; Feb. 1982; pp. 217-224.
International Preliminary Report on Patentability (Forms PCT/IB/338; PCT/IB/373; PCT/ISA/237 and PCT/IB/326) mailed May 23, 2013 for PCT/JP2011/074958.
Japanese and English version of International Preliminary Report on Patentability (Forms PCT/IB/338; PCT/IB/373; PCT/ISA/237 and PCT/IB/326).
Jorg Klingelhofer et al.; Amino-terminal domain of classic cadherins determines the specificity of the adhesive interactions; Journal of Cell Science; vol. 113; 2000; pp. 2829-2836.
Cathy Zhang et al.; PF-03732010: A Fully Human Monoclonal Antibody against . . . ; Clinical Cancer Research; vol. 16; No. 21; Sep. 9, 2010; pp. 5177-5188.
Cathy Zhang et al.; Preclinical characterization of PF-03732010: A human IgG1 mAb . . . ; AACR Meeting Abstracts, Apr. 16, 2008; pp. 1-2.

(Continued)

*Primary Examiner* — Maher Haddad
(74) *Attorney, Agent, or Firm* — Birch, Stewart, Kolasch & Birch, LLP

(57) ABSTRACT

It is an object of the present invention to provide an anti-cadherin antibody having a high internalization capacity and provide an anti-cadherin antibody-drug conjugate that effectively kills cadherin-expressing cancer cells with the use of such antibody. The present invention provides an anti-cadherin antibody which recognizes a cadherin domain 1 (EC1) of cadherin and exhibits a high internalization capacity.

20 Claims, 12 Drawing Sheets

(56) References Cited

OTHER PUBLICATIONS

Extended European Search Report dated Apr. 28, 2014, issued in corresponding European Patent Application No. 11836461.1.
European Office Action issued in European Patent Application No. 11 836 461.1 on Mar. 31, 2015.
Japanese Office Action for Appl. No. 2012-540965 dated Nov. 17, 2015 (w/ English translation).
European Office Action for Appl. No. 11836461.1 dated Jan. 29, 2016.

* cited by examiner

Fig. 1

```
E-cadherin_CDH1_    DWVIPPISCPENEKGPFPKNLVQIKSNKDKEGKVFYSITGQGADTPPVGVFIIERETGWL  60
P-cadherin_CDH3_    DWVVAPISVPENGKGPFPQRLNQLKSNKDRDTKIFYSITGPGADSPPEGVFAVEKETGWL  60
N-cadherin_CDH2_    DWVIPPINLPENSRGPFPQELVRIRSDRDKNLSLRYSVTGPGADGPPTGIFIINPISGQL  60

E-cadherin_CDH1_    KVTEPLDRERIATYTLFSHAVSSNGNAVEDPMEILITVTDQNDNKPEFTQEVFKGSVMEG 120
P-cadherin_CDH3_    LLNKPLDREEIAKYELFGHAVSENGASVEDPMNISIIVTDQNDHKPKFTQDTFRGSVLEG 120
N-cadherin_CDH2_    SVTKPLDREQIARFHLRAHAVDINGNQVENPIDIVINVIDMNDNRPEFLHQVVWNGTVPEG 120

E-cadherin_CDH1_    ALPGTSVMEVTATDADDDVNTYNAAIAYTILSQDPELPDKNMFTINRNTGVISVVTTGLD 180
P-cadherin_CDH3_    VLPGTSVMQVTATDEDDAIYTYNGVVAYSIHSQEPKDPHDLMFTIHRSTGTISVISSGLD 180
N-cadherin_CDH2_    SKPGTYVMTVTAIDADD-PNALNGMLRYRIVSQAPSTPSPNMFTINNETGDIITVAAGLD 179

E-cadherin_CDH1_    RESFPTYTLVVQAADLQGE---GLSTTATAVITVTDTNDNPPIFNPTTYKGQVPENEANV 237
P-cadherin_CDH3_    REKVPEYTLTIQATDMDGD---GSTTTAVAVVEILDANDNAPMFDPQKYEAHVPENAVGH 237
N-cadherin_CDH2_    REKVQQYTLIIQATDMEGNPTYGLSNTATAVITVTDVNDNPPEFTAMTFYGEVPENRVDI 239

E-cadherin_CDH1_    VITTLKVTDADAPNTPAWEAVYTILN-DDGGQFVVTTNPVNNDGILKTAKGLDFEAKQQY 296
P-cadherin_CDH3_    EVQRLTVTDLDAPNSPAWRATYLIMGGDDGDHFTITTHPESNQGILTTRKGLDFEAKNQH 297
N-cadherin_CDH2_    IVANLTVTDKDQPHTPAWNAVYRISGGDPTGRFAIQTDPNSNDGLVTVVKPIDFETNRMF 299

E-cadherin_CDH1_    ILHVAVTNVVPFEVSLTT---STATVTVDVLDVNEAPIFVPPEKRVEVSEDFGVGQEITS 353
P-cadherin_CDH3_    TLYVEVTNEAPFVLKLPT---STATIVVHVEDVNEAPVFVPPSKVVEVQEGIPTGEPVCV 354
N-cadherin_CDH2_    VLTVAAENQVPLAKGIQHPPQSTATVSVTVIDVNENPYFAPNPKIIRQEEGLHAGTMLTT 359

E-cadherin_CDH1_    YTAQEPDTFMEQKITYRIWRDTANWLEINPDTGAISTRAELDREDFEHVKNSTYTALIIA 413
P-cadherin_CDH3_    YTAEDPDK-ENQKISYRILRDPAGWLAMDPDSGQVTAVGTLDREDEQFVRNNIYEVMVLA 413
N-cadherin_CDH2_    FTAQDPDRYMQQNIRYTKLSDPANWLKIDPVNGQITTIAVLDRES-PNVKNNIYNATFLA 418

E-cadherin_CDH1_    TDNGSPVATGTGTLLLILSDVNDNAPIPEPRTIFFCER-NPKPQVINIIDADLPPNTSPF 472
P-cadherin_CDH3_    MDNGSPPTTGTGTLLLTLIDVNDHGPVPEPRQITICNQ-SPVRQVLNITDKDLSPHTSPF 472
N-cadherin_CDH2_    SDNGIPPMSGTGTLQIYLLDINDNAPQVLPQEAETCETPDPNSINITALDYDIDPNAGPF 478

E-cadherin_CDH1_    TAELTHG-ASANWTIQYNDPTQESIILKPK-MALEVGDYKINLKLMDNQN--KDQVTTLE 528
P-cadherin_CDH3_    QAQLTDD-SDIYWTAEVNE-EGDTVVLSLK-KFLKQDTYDVHLSLSDHGN--KEQLTVIR 527
N-cadherin_CDH2_    AFDLPLSPVTIKRNWTITRLNGDFAQLNLKIKFLEAGIYEVPIIITDSGNPPKSNISILR 538

E-cadherin_CDH1_    VSVCDCEGAAGVCRKAQPVEAGLQIPAILGILGGILALLILILLLLLFLRRR---AVVKE 585
P-cadherin_CDH3_    ATVCDCHGHVETC--PGPWKGGFILP----VLGAVLALLFLLLVLLLLVRKK---RKIKE 578
N-cadherin_CDH2_    VKVCQCDSNGDCTDVDRIVGAGLGTGAIIAILLCIIILLILVLMFVVWMKRRDKERQAKQ 598

E-cadherin_CDH1_    PLLPPEDDTRDNVYYYDEEGGGEEDQDFDLSQLHRG----LDARPEVT-RNDVAPTLMSV 640
P-cadherin_CDH3_    PLLLPEDDTRDNVFYYGEEGGGEEDQDYDITQLHRG----LEARPEVVLRNDVAPTIIPT 634
N-cadherin_CDH2_    LLIDPEDDVRDNILKYDEEGGGEEDQDYDLSQLQQPDTVEPDAIKPVGIRRMDERPIHAE 658

E-cadherin_CDH1_    PRYLPRPANPD--EIGNFIDENLKAADTDPTAPPYDSLLVFDYEGSGSEAASLSSLNSSE 698
P-cadherin_CDH3_    PMYRPRPANPD--EIGNFIIENLKAANTDPTAPPYDTLLVFDYEGSGSDAASLSSLTSSA 692
N-cadherin_CDH2_    PQYPVRSAAPHPGDIGDFINEGLKAADNDPTAPPYDSLLVFDYEGSGSTAGSLSSLNSSS 718

E-cadherin_CDH1_    SDKDQDYDYLNEWGNRFKKLADMYGGGEDD  728
P-cadherin_CDH3_    SDQDQDYDYLNEWGSRFKKLADMYGGGEDD  722
N-cadherin_CDH2_    SGGEQDYDYLNDWGPRFKKLADMYGGGDD-  747
```

Fig. 3
A
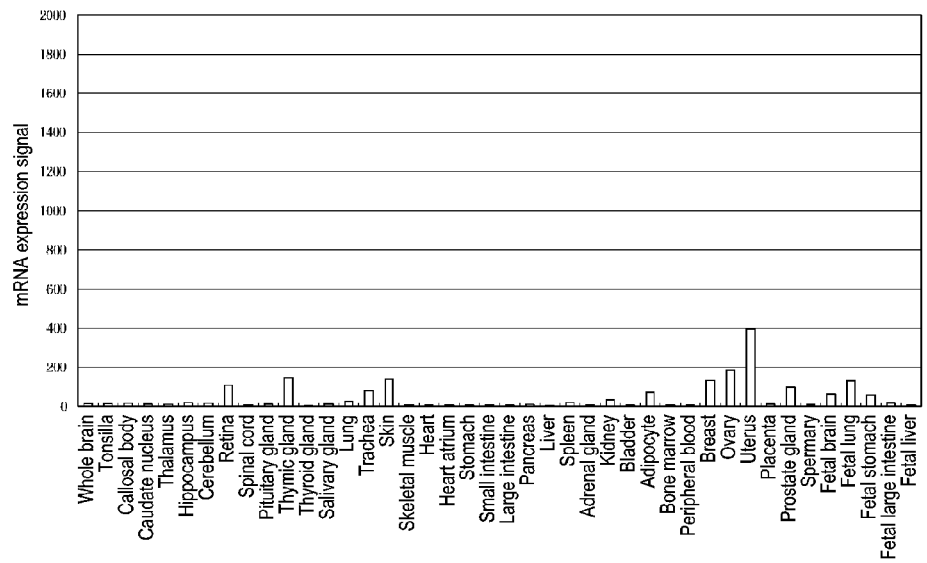
B
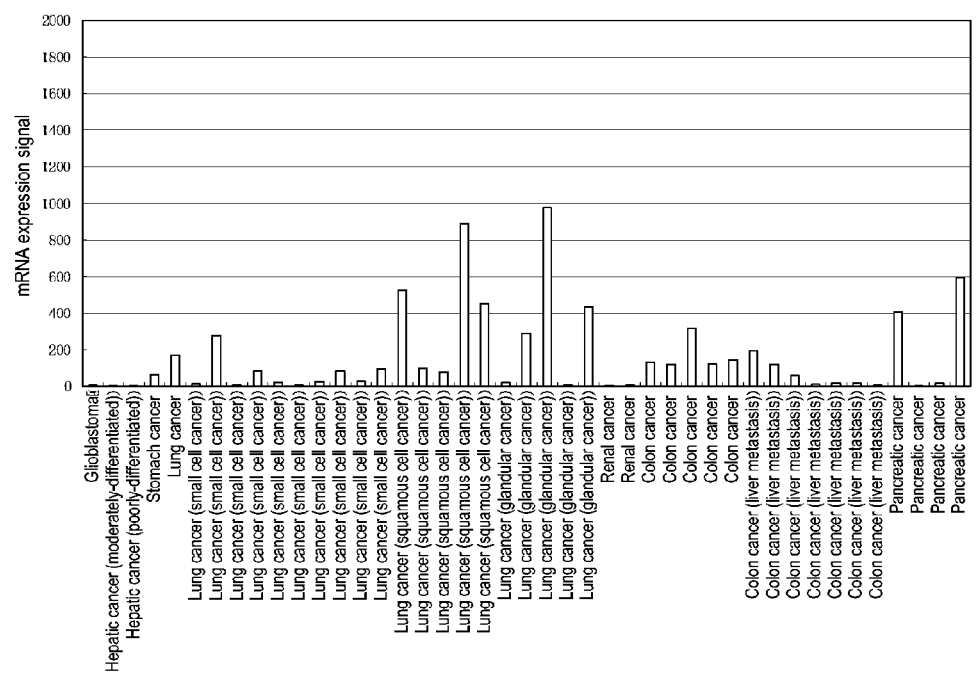

Fig. 7
A
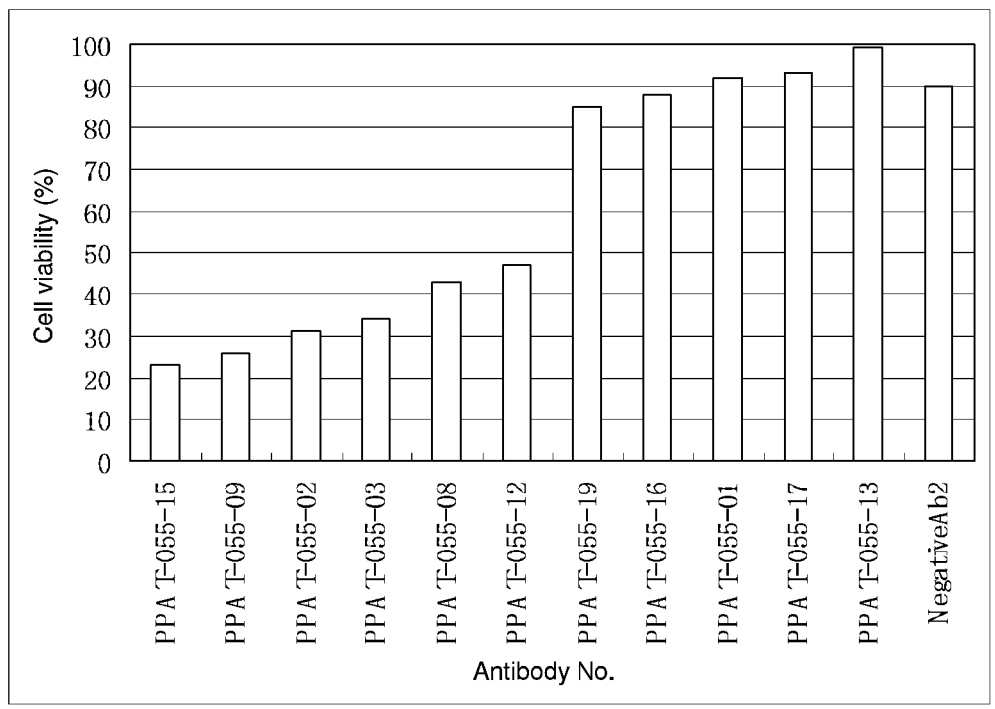
B
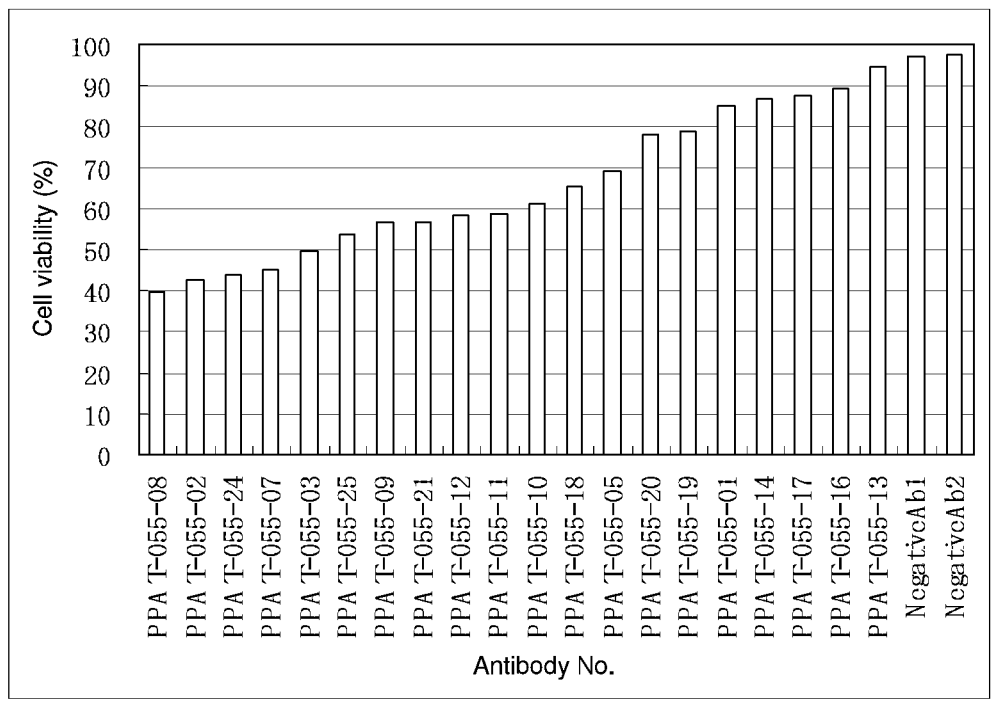

| Lane | Antibody No. |
|------|--------------|
| 1 | PPA T-055-01 |
| 2 | PPA T-055-02 |
| 3 | PPA T-055-03 |
| 5 | PPA T-055-05 |
| 7 | PPA T-055-07 |
| 8 | PPA T-055-08 |
| 9 | PPA T-055-09 |
| 10 | PPA T-055-10 |
| 11 | PPA T-055-11 |
| 12 | PPA T-055-12 |
| 13 | PPA T-055-13 |
| 14 | PPA T-055-14 |
| 15 | PPA T-055-15 |
| 16 | PPA T-055-16 |
| 17 | PPA T-055-17 |
| 18 | PPA T-055-18 |
| 19 | PPA T-055-19 |
| 20 | PPA T-055-20 |
| 21 | PPA T-055-21 |
| 27 | PPA T-055-25 |
| 28 | PPA T-055-24 |

Fig. 11
A
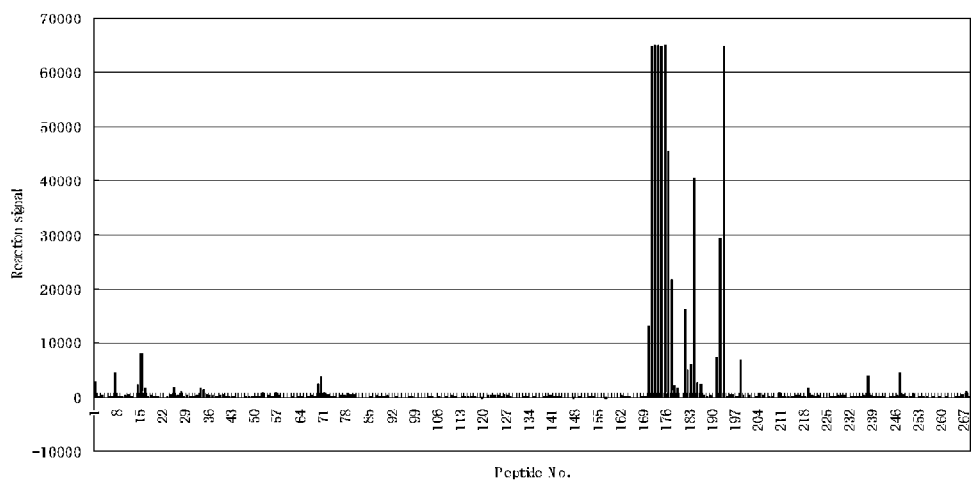
B
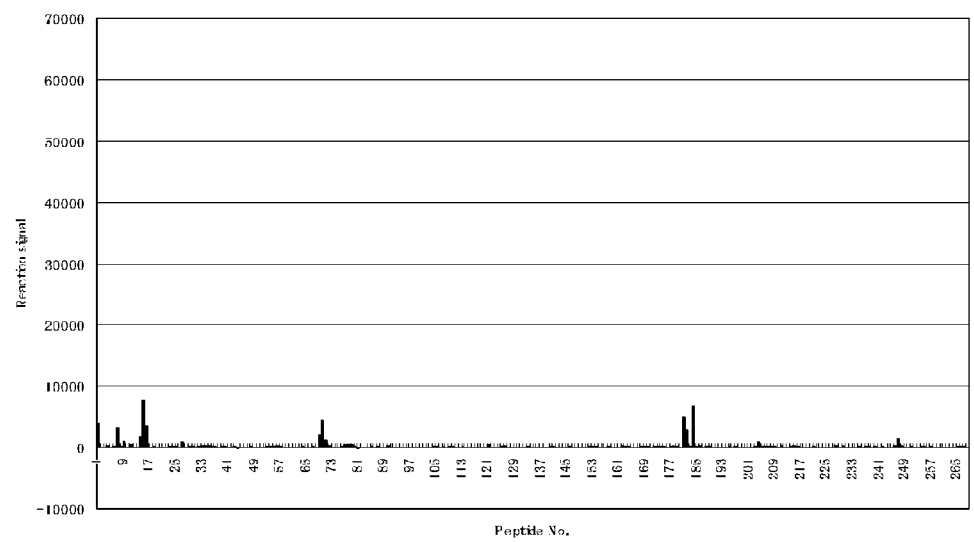

SEQUENCE LISTING

```
<160> NUMBER OF SEQ ID NOS: 61

<210> SEQ ID NO 1
<211> LENGTH: 2490
<212> TYPE: DNA
<213> ORGANISM: human
<220> FEATURE:
<221> NAME/KEY: CDS
<222> LOCATION: (1)..(2490)

<400> SEQUENCE: 1 atg ggg ctc cct cgt gga cct ctc gcg tct ctc ctc ctt ctc cag gtt       48
Met Gly Leu Pro Arg Gly Pro Leu Ala Ser Leu Leu Leu Leu Gln Val
1               5                   10                  15 tgc tgg ctg cag tgc gcg gcc tcc gag ccg tgc cgg gcg gtc ttc agg       96
Cys Trp Leu Gln Cys Ala Ala Ser Glu Pro Cys Arg Ala Val Phe Arg
            20                  25                  30 gag gct gaa gtg acc ttg gag gcg gga ggc gcg gag cag gag ccc ggc      144
Glu Ala Glu Val Thr Leu Glu Ala Gly Gly Ala Glu Gln Glu Pro Gly
        35                  40                  45 cag gcg ctg ggg aaa gta ttc atg ggc tgc cct ggg caa gag cca gct      192
Gln Ala Leu Gly Lys Val Phe Met Gly Cys Pro Gly Gln Glu Pro Ala
    50                  55                  60 ctg ttt agc act gat aat gat gac ttc act gtg cgg aat ggc gag aca      240
Leu Phe Ser Thr Asp Asn Asp Asp Phe Thr Val Arg Asn Gly Glu Thr
65                  70                  75                  80 gtc cag gaa aga agg tca ctg aag gaa agg aat cca ttg aag atc ttc      288
Val Gln Glu Arg Arg Ser Leu Lys Glu Arg Asn Pro Leu Lys Ile Phe
                85                  90                  95 cca tcc aaa cgt atc tta cga aga cac aag aga gat tgg gtg gtt gct      336
Pro Ser Lys Arg Ile Leu Arg Arg His Lys Arg Asp Trp Val Val Ala
            100                 105                 110 cca ata tct gtc cct gaa aat ggc aag ggt ccc ttc ccc cag aga ctg      384
Pro Ile Ser Val Pro Glu Asn Gly Lys Gly Pro Phe Pro Gln Arg Leu
        115                 120                 125 aat cag ctc aag tct aat aaa gat aga gac acc aag att ttc tac agc      432
Asn Gln Leu Lys Ser Asn Lys Asp Arg Asp Thr Lys Ile Phe Tyr Ser
    130                 135                 140 atc acg ggg ccg ggg gca gac agc ccc cct gag ggt gtc ttc gct gta      480
Ile Thr Gly Pro Gly Ala Asp Ser Pro Pro Glu Gly Val Phe Ala Val
145                 150                 155                 160 gag aag gag aca ggc tgg ttg ttg ttg aat aag cca ctg gac cgg gag      528
Glu Lys Glu Thr Gly Trp Leu Leu Leu Asn Lys Pro Leu Asp Arg Glu
                165                 170                 175 gag att gcc aag tat gag ctc ttt ggc cac gct gtg tca gag aat ggt      576
Glu Ile Ala Lys Tyr Glu Leu Phe Gly His Ala Val Ser Glu Asn Gly
            180                 185                 190 gcc tca gtg gag gac ccc atg aac atc tcc atc atc gtg acc gac cag      624
Ala Ser Val Glu Asp Pro Met Asn Ile Ser Ile Ile Val Thr Asp Gln
        195                 200                 205 aat gac cac aag ccc aag ttt acc cag gac acc ttc cga ggg agt gtc      672
Asn Asp His Lys Pro Lys Phe Thr Gln Asp Thr Phe Arg Gly Ser Val
    210                 215                 220
```

-continued

| | | |
|---|---|---|
| tta gag gga gtc cta cca ggt act tct gtg atg cag gtg aca gcc acg<br>Leu Glu Gly Val Leu Pro Gly Thr Ser Val Met Gln Val Thr Ala Thr<br>225                         230                     235                  240 | 720 |
| gat gag gat gat gcc atc tac acc tac aat ggg gtg gtt gct tac tcc<br>Asp Glu Asp Asp Ala Ile Tyr Thr Tyr Asn Gly Val Val Ala Tyr Ser<br>                   245                     250                     255 | 768 |
| atc cat agc caa gaa cca aag gac cca cac gac ctc atg ttc acc att<br>Ile His Ser Gln Glu Pro Lys Asp Pro His Asp Leu Met Phe Thr Ile<br>         260                     265                     270 | 816 |
| cac cgg agc aca ggc acc atc agc gtc atc tcc agt ggc ctg gac cgg<br>His Arg Ser Thr Gly Thr Ile Ser Val Ile Ser Ser Gly Leu Asp Arg<br>275                         280                     285 | 864 |
| gaa aaa gtc cct gag tac aca ctg acc atc cag gcc aca gac atg gat<br>Glu Lys Val Pro Glu Tyr Thr Leu Thr Ile Gln Ala Thr Asp Met Asp<br>         290                     295                     300 | 912 |
| ggg gac ggc tcc acc acc acg gca gtg gca gta gtg gag atc ctt gat<br>Gly Asp Gly Ser Thr Thr Thr Ala Val Ala Val Val Glu Ile Leu Asp<br>305                         310                     315                  320 | 960 |
| gcc aat gac aat gct ccc atg ttt gac ccc cag aag tac gag gcc cat<br>Ala Asn Asp Asn Ala Pro Met Phe Asp Pro Gln Lys Tyr Glu Ala His<br>                   325                     330                     335 | 1008 |
| gtg cct gag aat gca gtg ggc cat gag gtg cag agg ctg acg gtc act<br>Val Pro Glu Asn Ala Val Gly His Glu Val Gln Arg Leu Thr Val Thr<br>         340                     345                     350 | 1056 |
| gat ctg gac gcc ccc aac tca cca gcg tgg cgt gcc acc tac ctt atc<br>Asp Leu Asp Ala Pro Asn Ser Pro Ala Trp Arg Ala Thr Tyr Leu Ile<br>355                         360                     365 | 1104 |
| atg ggc ggt gac gac ggg gac cat ttt acc atc acc acc cac cct gag<br>Met Gly Gly Asp Asp Gly Asp His Phe Thr Ile Thr Thr His Pro Glu<br>         370                     375                     380 | 1152 |
| agc aac cag ggc atc ctg aca acc agg aag ggt ttg gat ttt gag gcc<br>Ser Asn Gln Gly Ile Leu Thr Thr Arg Lys Gly Leu Asp Phe Glu Ala<br>385                         390                     395                  400 | 1200 |
| aaa aac cag cac acc ctg tac gtt gaa gtg acc aac gag gcc cct ttt<br>Lys Asn Gln His Thr Leu Tyr Val Glu Val Thr Asn Glu Ala Pro Phe<br>                   405                     410                     415 | 1248 |
| gtg ctg aag ctc cca acc tcc aca gcc acc ata gtg gtc cac gtg gag<br>Val Leu Lys Leu Pro Thr Ser Thr Ala Thr Ile Val Val His Val Glu<br>               420                     425                     430 | 1296 |
| gat gtg aat gag gca cct gtg ttt gtc cca ccc tcc aaa gtc gtt gag<br>Asp Val Asn Glu Ala Pro Val Phe Val Pro Pro Ser Lys Val Val Glu<br>               435                     440                     445 | 1344 |
| gtc cag gag ggc atc ccc act ggg gag cct gtg tgt gtc tac act gca<br>Val Gln Glu Gly Ile Pro Thr Gly Glu Pro Val Cys Val Tyr Thr Ala<br>450                         455                     460 | 1392 |
| gaa gac cct gac aag gag aat caa aag atc agc tac cgc atc ctg aga<br>Glu Asp Pro Asp Lys Glu Asn Gln Lys Ile Ser Tyr Arg Ile Leu Arg<br>465                         470                     475                  480 | 1440 |
| gac cca gca ggg tgg cta gcc atg gac cca gac agt ggg cag gtc aca<br>Asp Pro Ala Gly Trp Leu Ala Met Asp Pro Asp Ser Gly Gln Val Thr<br>                   485                     490                     495 | 1488 |
| gct gtg ggc acc ctc gac cgt gag gat gag cag ttt gtg agg aac aac<br>Ala Val Gly Thr Leu Asp Arg Glu Asp Glu Gln Phe Val Arg Asn Asn<br>         500                     505                     510 | 1536 |
| atc tat gaa gtc atg gtc ttg gcc atg gac aat gga agc cct ccc acc<br>Ile Tyr Glu Val Met Val Leu Ala Met Asp Asn Gly Ser Pro Pro Thr<br>               515                     520                     525 | 1584 |
| act ggc acg gga acc ctt ctg cta aca ctg att gat gtc aat gac cat<br>Thr Gly Thr Gly Thr Leu Leu Leu Thr Leu Ile Asp Val Asn Asp His | 1632 |

```
                530                 535                 540
ggc cca gtc cct gag ccc cgt cag atc acc atc tgc aac caa agc cct      1680
Gly Pro Val Pro Glu Pro Arg Gln Ile Thr Ile Cys Asn Gln Ser Pro
545                 550                 555                 560 gtg cgc cag gtg ctg aac atc acg gac aag gac ctg tct ccc cac acc      1728
Val Arg Gln Val Leu Asn Ile Thr Asp Lys Asp Leu Ser Pro His Thr
                565                 570                 575 tcc cct ttc cag gcc cag ctc aca gat gac tca gac atc tac tgg acg      1776
Ser Pro Phe Gln Ala Gln Leu Thr Asp Asp Ser Asp Ile Tyr Trp Thr
            580                 585                 590 gca gag gtc aac gag gaa ggt gac aca gtg gtc ttg tcc ctg aag aag      1824
Ala Glu Val Asn Glu Glu Gly Asp Thr Val Val Leu Ser Leu Lys Lys
        595                 600                 605 ttc ctg aag cag gat aca tat gac gtg cac ctt tct ctg tct gac cat      1872
Phe Leu Lys Gln Asp Thr Tyr Asp Val His Leu Ser Leu Ser Asp His
    610                 615                 620 ggc aac aaa gag cag ctg acg gtg atc agg gcc act gtg tgc gac tgc      1920
Gly Asn Lys Glu Gln Leu Thr Val Ile Arg Ala Thr Val Cys Asp Cys
625                 630                 635                 640 cat ggc cat gtc gaa acc tgc cct gga ccc tgg aag gga ggt ttc atc      1968
His Gly His Val Glu Thr Cys Pro Gly Pro Trp Lys Gly Gly Phe Ile
                645                 650                 655 ctc cct gtg ctg ggg gct gtc ctg gct ctg ctg ttc ctg ctg ctg gtg      2016
Leu Pro Val Leu Gly Ala Val Leu Ala Leu Leu Phe Leu Leu Leu Val
            660                 665                 670 ctg ctt ttg ttg gtg aga aag aag cgg aag atc aag gag ccc ctc cta      2064
Leu Leu Leu Leu Val Arg Lys Lys Arg Lys Ile Lys Glu Pro Leu Leu
        675                 680                 685 ctc cca gaa gat gac acc cgt gac aac gtc ttc tac tat ggc gaa gag      2112
Leu Pro Glu Asp Asp Thr Arg Asp Asn Val Phe Tyr Tyr Gly Glu Glu
    690                 695                 700 ggg ggt ggc gaa gag gac cag gac tat gac atc acc cag ctc cac cga      2160
Gly Gly Gly Glu Glu Asp Gln Asp Tyr Asp Ile Thr Gln Leu His Arg
705                 710                 715                 720 ggt ctg gag gcc agg ccg gag gtg gtt ctc cgc aat gac gtg gca cca      2208
Gly Leu Glu Ala Arg Pro Glu Val Val Leu Arg Asn Asp Val Ala Pro
                725                 730                 735 acc atc atc ccg aca ccc atg tac cgt cct cgg cca gcc aac cca gat      2256
Thr Ile Ile Pro Thr Pro Met Tyr Arg Pro Arg Pro Ala Asn Pro Asp
            740                 745                 750 gaa atc ggc aac ttt ata att gag aac ctg aag gcg gct aac aca gac      2304
Glu Ile Gly Asn Phe Ile Ile Glu Asn Leu Lys Ala Ala Asn Thr Asp
        755                 760                 765 ccc aca gcc ccg ccc tac gac acc ctc ttg gtg ttc gac tat gag ggc      2352
Pro Thr Ala Pro Pro Tyr Asp Thr Leu Leu Val Phe Asp Tyr Glu Gly
    770                 775                 780 agc ggc tcc gac gcc gcg tcc ctg agc tcc ctc acc tcc tcc gcc tcc      2400
Ser Gly Ser Asp Ala Ala Ser Leu Ser Ser Leu Thr Ser Ser Ala Ser
785                 790                 795                 800 gac caa gac caa gat tac gat tat ctg aac gag tgg ggc agc cgc ttc      2448
Asp Gln Asp Gln Asp Tyr Asp Tyr Leu Asn Glu Trp Gly Ser Arg Phe
                805                 810                 815 aag aag ctg gca gac atg tac ggt ggc ggg gag gac gac tag              2490
Lys Lys Leu Ala Asp Met Tyr Gly Gly Gly Glu Asp Asp
            820                 825

<210> SEQ ID NO 2
<211> LENGTH: 829
<212> TYPE: PRT
<213> ORGANISM: human
```

<400> SEQUENCE: 2

```
Met Gly Leu Pro Arg Gly Pro Leu Ala Ser Leu Leu Leu Leu Gln Val
1               5                   10                  15

Cys Trp Leu Gln Cys Ala Ala Ser Glu Pro Cys Arg Ala Val Phe Arg
            20                  25                  30

Glu Ala Glu Val Thr Leu Glu Ala Gly Gly Ala Glu Gln Glu Pro Gly
        35                  40                  45

Gln Ala Leu Gly Lys Val Phe Met Gly Cys Pro Gly Gln Glu Pro Ala
    50                  55                  60

Leu Phe Ser Thr Asp Asn Asp Asp Phe Thr Val Arg Asn Gly Glu Thr
65                  70                  75                  80

Val Gln Glu Arg Arg Ser Leu Lys Glu Arg Asn Pro Leu Lys Ile Phe
                85                  90                  95

Pro Ser Lys Arg Ile Leu Arg Arg His Lys Arg Asp Trp Val Val Ala
            100                 105                 110

Pro Ile Ser Val Pro Glu Asn Gly Lys Gly Pro Phe Pro Gln Arg Leu
        115                 120                 125

Asn Gln Leu Lys Ser Asn Lys Asp Arg Asp Thr Lys Ile Phe Tyr Ser
    130                 135                 140

Ile Thr Gly Pro Gly Ala Asp Ser Pro Pro Glu Gly Val Phe Ala Val
145                 150                 155                 160

Glu Lys Glu Thr Gly Trp Leu Leu Leu Asn Lys Pro Leu Asp Arg Glu
                165                 170                 175

Glu Ile Ala Lys Tyr Glu Leu Phe Gly His Ala Val Ser Glu Asn Gly
            180                 185                 190

Ala Ser Val Glu Asp Pro Met Asn Ile Ser Ile Ile Val Thr Asp Gln
        195                 200                 205

Asn Asp His Lys Pro Lys Phe Thr Gln Asp Thr Phe Arg Gly Ser Val
    210                 215                 220

Leu Glu Gly Val Leu Pro Gly Thr Ser Val Met Gln Val Thr Ala Thr
225                 230                 235                 240

Asp Glu Asp Asp Ala Ile Tyr Thr Tyr Asn Gly Val Val Ala Tyr Ser
                245                 250                 255

Ile His Ser Gln Glu Pro Lys Asp Pro His Asp Leu Met Phe Thr Ile
            260                 265                 270

His Arg Ser Thr Gly Thr Ile Ser Val Ile Ser Ser Gly Leu Asp Arg
        275                 280                 285

Glu Lys Val Pro Glu Tyr Thr Leu Thr Ile Gln Ala Thr Asp Met Asp
    290                 295                 300

Gly Asp Gly Ser Thr Thr Thr Ala Val Ala Val Val Glu Ile Leu Asp
305                 310                 315                 320

Ala Asn Asp Asn Ala Pro Met Phe Asp Pro Gln Lys Tyr Glu Ala His
                325                 330                 335

Val Pro Glu Asn Ala Val Gly His Glu Val Gln Arg Leu Thr Val Thr
            340                 345                 350

Asp Leu Asp Ala Pro Asn Ser Pro Ala Trp Arg Ala Thr Tyr Leu Ile
        355                 360                 365

Met Gly Gly Asp Asp Gly Asp His Phe Thr Ile Thr Thr His Pro Glu
    370                 375                 380

Ser Asn Gln Gly Ile Leu Thr Thr Arg Lys Gly Leu Asp Phe Glu Ala
385                 390                 395                 400

Lys Asn Gln His Thr Leu Tyr Val Glu Val Thr Asn Glu Ala Pro Phe
```

```
            405                 410                 415
Val Leu Lys Leu Pro Thr Ser Thr Ala Thr Ile Val Val His Val Glu
            420                 425                 430

Asp Val Asn Glu Ala Pro Val Phe Val Pro Pro Ser Lys Val Val Glu
            435                 440                 445

Val Gln Glu Gly Ile Pro Thr Gly Glu Pro Val Cys Val Tyr Thr Ala
    450                 455                 460

Glu Asp Pro Asp Lys Glu Asn Gln Lys Ile Ser Tyr Arg Ile Leu Arg
465                 470                 475                 480

Asp Pro Ala Gly Trp Leu Ala Met Asp Pro Asp Ser Gly Gln Val Thr
                485                 490                 495

Ala Val Gly Thr Leu Asp Arg Glu Asp Glu Gln Phe Val Arg Asn Asn
            500                 505                 510

Ile Tyr Glu Val Met Val Leu Ala Met Asp Asn Gly Ser Pro Pro Thr
            515                 520                 525

Thr Gly Thr Gly Thr Leu Leu Leu Thr Leu Ile Asp Val Asn Asp His
            530                 535                 540

Gly Pro Val Pro Glu Pro Arg Gln Ile Thr Ile Cys Asn Gln Ser Pro
545                 550                 555                 560

Val Arg Gln Val Leu Asn Ile Thr Asp Lys Asp Leu Ser Pro His Thr
                565                 570                 575

Ser Pro Phe Gln Ala Gln Leu Thr Asp Asp Ser Asp Ile Tyr Trp Thr
            580                 585                 590

Ala Glu Val Asn Glu Glu Gly Asp Thr Val Val Leu Ser Leu Lys Lys
            595                 600                 605

Phe Leu Lys Gln Asp Thr Tyr Asp Val His Leu Ser Leu Ser Asp His
610                 615                 620

Gly Asn Lys Glu Gln Leu Thr Val Ile Arg Ala Thr Val Cys Asp Cys
625                 630                 635                 640

His Gly His Val Glu Thr Cys Pro Gly Pro Trp Lys Gly Gly Phe Ile
                645                 650                 655

Leu Pro Val Leu Gly Ala Val Leu Ala Leu Leu Phe Leu Leu Leu Val
            660                 665                 670

Leu Leu Leu Leu Val Arg Lys Lys Arg Lys Ile Lys Glu Pro Leu Leu
            675                 680                 685

Leu Pro Glu Asp Asp Thr Arg Asp Asn Val Phe Tyr Tyr Gly Glu Glu
            690                 695                 700

Gly Gly Gly Glu Glu Asp Gln Asp Tyr Asp Ile Thr Gln Leu His Arg
705                 710                 715                 720

Gly Leu Glu Ala Arg Pro Glu Val Val Leu Arg Asn Asp Val Ala Pro
                725                 730                 735

Thr Ile Ile Pro Thr Pro Met Tyr Arg Pro Arg Pro Ala Asn Pro Asp
            740                 745                 750

Glu Ile Gly Asn Phe Ile Ile Glu Asn Leu Lys Ala Ala Asn Thr Asp
            755                 760                 765

Pro Thr Ala Pro Pro Tyr Asp Thr Leu Leu Val Phe Asp Tyr Glu Gly
    770                 775                 780

Ser Gly Ser Asp Ala Ala Ser Leu Ser Ser Leu Thr Ser Ser Ala Ser
785                 790                 795                 800

Asp Gln Asp Gln Asp Tyr Asp Tyr Leu Asn Glu Trp Gly Ser Arg Phe
                805                 810                 815

Lys Lys Leu Ala Asp Met Tyr Gly Gly Gly Glu Asp Asp
            820                 825
```

<210> SEQ ID NO 3
<211> LENGTH: 2040
<212> TYPE: DNA
<213> ORGANISM: human

<400> SEQUENCE: 3

```
agtggcgtcg gaactgcaaa gcacctgtga gcttgcggaa gtcagttcag actccagccc      60
gctccagccc ggcccgaccc gaccgcaccc ggcgcctgcc ctcgctcggc gtccccggcc     120
agccatgggc ccttggagcc gcagcctctc ggcgctgctg ctgctgctgc aggtctcctc     180
ttggctctgc caggagccgg agccctgcca ccctggcttt gacgccgaga gctacacgtt     240
cacggtgccc cggcgccacc tggagagagg ccgcgtcctg ggcagagtga attttgaaga     300
ttgcaccggt cgacaaagga cagcctattt ttccctcgac acccgattca agtgggcac     360
agatggtgtg attacagtca aaaggcctct acggtttcat aacccacaga tccatttctt     420
ggtctacgcc tgggactcca cctacagaaa gttttccacc aaagtcacgc tgaatacagt     480
ggggcaccac caccgccccc cgccccatca ggcctccgtt tctggaatcc aagcagaatt     540
gctcacattt cccaactcct ctcctggcct cagaagacag aagagagact gggttattcc     600
tcccatcagc tgcccagaaa atgaaaaagg cccatttcct aaaaacctgg ttcagatcaa     660
atccaacaaa gacaagaag gcaaggtttt ctacagcatc actggccaag agctgacac     720
accccctgtt ggtgtcttta ttattgaaag agaaacagga tggctgaagg tgacagagcc     780
tctggataga gaacgcattg ccacatacac tctcttctct cacgctgtgt catccaacgg     840
gaatgcagtt gaggatccaa tggagatttt gatcacggta accgatcaga atgacaacaa     900
gcccgaattc acccaggagg tctttaaggg gtctgtcatg gaaggtgctc ttccaggaac     960
ctctgtgatg gaggtcacag ccacagacgc ggacgatgat gtgaacacct acaatgccgc    1020
catcgcttac accatcctca gccaagatcc tgagctccct gacaaaaata tgttcaccat    1080
taacagggaac acaggagtca tcagtgtggt caccactggg ctggaccgag agagtttccc    1140
tacgtatacc ctggtggttc aagctgctga ccttcaaggt gagggggttaa gcacaacagc    1200
aacagctgtg atcacagtca ctgacaccaa cgataatcct ccgatcttca atcccaccac    1260
gtacaagggt caggtgcctg agaacgaggc taacgtcgta atcaccacac tgaaagtgac    1320
tgatgctgat gccccccaata ccccagcgtg ggaggctgta tacaccatat gaatgatga    1380
tggtggacaa tttgtcgtca ccacaaatcc agtgaacaac gatggcattt tgaaaacagc    1440
aaagggcttg gattttgagg ccaagcagca gtacattcta cacgtagcag tgacgaatgt    1500
ggtacctttt gaggtctctc tcaccacctc cacagccacc gtcaccgtgg atgtgctgga    1560
tgtgaatgaa gcccccatct ttgtgcctcc tgaaaagaga gtggaagtgt ccgaggactt    1620
tggcgtgggc caggaaatca catcctacac tgcccaggag ccagacacat ttatggaaca    1680
gaaaataaca tatcggattt ggagagacac tgccaactgg ctgagattaa tccggacac    1740
tggtgccatt tccactcggg ctgagctgga cagggaggat tttgagcacg tgaagaacag    1800
cacgtacaca gccctaatca tagctacaga caatggttct ccagttgcta ctggaacagg    1860
gacacttctg ctgatcctgt ctgatgtgaa tgacaacgcc cccatccag aacctcgaac    1920
tatattcttc tgtgagagga atccaaagcc tcaggtcata aacatcattg atgcagacct    1980
tcctcccaat acatctcccct tcacagcaga actaacacac ggggcgagtg ccaactggac    2040
```

<210> SEQ ID NO 4

-continued

```
<211> LENGTH: 882
<212> TYPE: PRT
<213> ORGANISM: human

<400> SEQUENCE: 4

Met Gly Pro Trp Ser Arg Ser Leu Ser Ala Leu Leu Leu Leu Leu Gln
1               5                   10                  15

Val Ser Ser Trp Leu Cys Gln Glu Pro Glu Pro Cys His Pro Gly Phe
            20                  25                  30

Asp Ala Glu Ser Tyr Thr Phe Thr Val Pro Arg Arg His Leu Glu Arg
        35                  40                  45

Gly Arg Val Leu Gly Arg Val Asn Phe Glu Asp Cys Thr Gly Arg Gln
    50                  55                  60

Arg Thr Ala Tyr Phe Ser Leu Asp Thr Arg Phe Lys Val Gly Thr Asp
65                  70                  75                  80

Gly Val Ile Thr Val Lys Arg Pro Leu Arg Phe His Asn Pro Gln Ile
                85                  90                  95

His Phe Leu Val Tyr Ala Trp Asp Ser Thr Tyr Arg Lys Phe Ser Thr
            100                 105                 110

Lys Val Thr Leu Asn Thr Val Gly His His Arg Pro Pro Pro His
        115                 120                 125

Gln Ala Ser Val Ser Gly Ile Gln Ala Glu Leu Leu Thr Phe Pro Asn
    130                 135                 140

Ser Ser Pro Gly Leu Arg Arg Gln Lys Arg Asp Trp Val Ile Pro Pro
145                 150                 155                 160

Ile Ser Cys Pro Glu Asn Glu Lys Gly Pro Phe Pro Lys Asn Leu Val
                165                 170                 175

Gln Ile Lys Ser Asn Lys Asp Lys Glu Gly Lys Val Phe Tyr Ser Ile
            180                 185                 190

Thr Gly Gln Gly Ala Asp Thr Pro Pro Val Gly Val Phe Ile Ile Glu
        195                 200                 205

Arg Glu Thr Gly Trp Leu Lys Val Thr Glu Pro Leu Asp Arg Glu Arg
    210                 215                 220

Ile Ala Thr Tyr Thr Leu Phe Ser His Ala Val Ser Ser Asn Gly Asn
225                 230                 235                 240

Ala Val Glu Asp Pro Met Glu Ile Leu Ile Thr Val Thr Asp Gln Asn
                245                 250                 255

Asp Asn Lys Pro Glu Phe Thr Gln Glu Val Phe Lys Gly Ser Val Met
            260                 265                 270

Glu Gly Ala Leu Pro Gly Thr Ser Val Met Glu Val Thr Ala Thr Asp
        275                 280                 285

Ala Asp Asp Asp Val Asn Thr Tyr Asn Ala Ala Ile Ala Tyr Thr Ile
    290                 295                 300

Leu Ser Gln Asp Pro Glu Leu Pro Asp Lys Asn Met Phe Thr Ile Asn
305                 310                 315                 320

Arg Asn Thr Gly Val Ile Ser Val Val Thr Thr Gly Leu Asp Arg Glu
                325                 330                 335

Ser Phe Pro Thr Tyr Thr Leu Val Val Gln Ala Ala Asp Leu Gln Gly
            340                 345                 350

Glu Gly Leu Ser Thr Thr Ala Thr Ala Val Ile Thr Val Thr Asp Thr
        355                 360                 365

Asn Asp Asn Pro Pro Ile Phe Asn Pro Thr Thr Tyr Lys Gly Gln Val
    370                 375                 380

Pro Glu Asn Glu Ala Asn Val Val Ile Thr Thr Leu Lys Val Thr Asp
```

```
            385                 390                 395                 400
        Ala Asp Ala Pro Asn Thr Pro Ala Trp Glu Ala Val Tyr Thr Ile Leu
                        405                 410                 415
        Asn Asp Asp Gly Gly Gln Phe Val Val Thr Thr Asn Pro Val Asn Asn
                        420                 425                 430
        Asp Gly Ile Leu Lys Thr Ala Lys Gly Leu Asp Phe Glu Ala Lys Gln
                        435                 440                 445
        Gln Tyr Ile Leu His Val Ala Val Thr Asn Val Val Pro Phe Glu Val
                        450                 455                 460
        Ser Leu Thr Thr Ser Thr Ala Thr Val Thr Val Asp Val Leu Asp Val
        465                 470                 475                 480
        Asn Glu Ala Pro Ile Phe Val Pro Pro Glu Lys Arg Val Glu Val Ser
                        485                 490                 495
        Glu Asp Phe Gly Val Gly Gln Glu Ile Thr Ser Tyr Thr Ala Gln Glu
                        500                 505                 510
        Pro Asp Thr Phe Met Glu Gln Lys Ile Thr Tyr Arg Ile Trp Arg Asp
                        515                 520                 525
        Thr Ala Asn Trp Leu Glu Ile Asn Pro Asp Thr Gly Ala Ile Ser Thr
                        530                 535                 540
        Arg Ala Glu Leu Asp Arg Glu Asp Phe Glu His Val Lys Asn Ser Thr
        545                 550                 555                 560
        Tyr Thr Ala Leu Ile Ile Ala Thr Asp Asn Gly Ser Pro Val Ala Thr
                        565                 570                 575
        Gly Thr Gly Thr Leu Leu Leu Ile Leu Ser Asp Val Asn Asp Asn Ala
                        580                 585                 590
        Pro Ile Pro Glu Pro Arg Thr Ile Phe Phe Cys Glu Arg Asn Pro Lys
                        595                 600                 605
        Pro Gln Val Ile Asn Ile Ile Asp Ala Asp Leu Pro Pro Asn Thr Ser
                        610                 615                 620
        Pro Phe Thr Ala Glu Leu Thr His Gly Ala Ser Ala Asn Trp Thr Ile
        625                 630                 635                 640
        Gln Tyr Asn Asp Pro Thr Gln Glu Ser Ile Ile Leu Lys Pro Lys Met
                        645                 650                 655
        Ala Leu Glu Val Gly Asp Tyr Lys Ile Asn Leu Lys Leu Met Asp Asn
                        660                 665                 670
        Gln Asn Lys Asp Gln Val Thr Thr Leu Glu Val Ser Val Cys Asp Cys
                        675                 680                 685
        Glu Gly Ala Ala Gly Val Cys Arg Lys Ala Gln Pro Val Glu Ala Gly
                        690                 695                 700
        Leu Gln Ile Pro Ala Ile Leu Gly Ile Leu Gly Gly Ile Leu Ala Leu
        705                 710                 715                 720
        Leu Ile Leu Ile Leu Leu Leu Leu Phe Leu Arg Arg Arg Ala Val
                        725                 730                 735
        Val Lys Glu Pro Leu Leu Pro Pro Glu Asp Asp Thr Arg Asp Asn Val
                        740                 745                 750
        Tyr Tyr Tyr Asp Glu Glu Gly Gly Glu Glu Asp Gln Asp Phe Asp
                        755                 760                 765
        Leu Ser Gln Leu His Arg Gly Leu Asp Ala Arg Pro Glu Val Thr Arg
                        770                 775                 780
        Asn Asp Val Ala Pro Thr Leu Met Ser Val Pro Arg Tyr Leu Pro Arg
        785                 790                 795                 800
        Pro Ala Asn Pro Asp Glu Ile Gly Asn Phe Ile Asp Glu Asn Leu Lys
                        805                 810                 815
```

```
Ala Ala Asp Thr Asp Pro Thr Ala Pro Pro Tyr Asp Ser Leu Leu Val
            820                 825                 830

Phe Asp Tyr Glu Gly Ser Gly Ser Glu Ala Ala Ser Leu Ser Ser Leu
        835                 840                 845

Asn Ser Ser Glu Ser Asp Lys Asp Gln Asp Tyr Asp Tyr Leu Asn Glu
850                 855                 860

Trp Gly Asn Arg Phe Lys Lys Leu Ala Asp Met Tyr Gly Gly Gly Glu
865                 870                 875                 880

Asp Asp

<210> SEQ ID NO 5
<211> LENGTH: 4380
<212> TYPE: DNA
<213> ORGANISM: human

<400> SEQUENCE: 5
ggggagcgcc atccgctcca cttccacctc cacatcctcc accggccaag gtccccgccg      60
ctgcatccct cgcggcttcc gctgcgctcc gggccggagc cgagccgcct gcgctgccac     120
agcagccgcc tccacacact cgcagacgct cacacgctct ccctccctgt tccccgccc      180 cctccccagc tccttgatct ctgggtctgt tttattactc ctggtgcgag tcccgcggac     240
tccgcggccc gctatttgtc atcagctcgc tctccattgg cggggagcgg agagcagcga     300
agaagggggt ggggagggga ggggaaggga aggggggtgga aactgcctgg agccgtttct     360
ccgcgccgct gttggtgctg ccgctgcctc ctcctcctcc gccgccgccg ccgccgccgc     420
cgcctcctcc ggctcttcgc tcggcccctc tccgcctcca tgtgccggat agcgggagcg     480
ctgcggaccc tgctgccgct gctggcggcc ctgcttcagg cgtctgtaga ggcttctggt     540
gaaatcgcat tatgcaagac tggatttcct gaagatgttt acagtgcagt cttatcgaag     600
gatgtgcatg aaggacagcc tcttctcaat gtgaagtta gcaactgcaa tggaaaaaga     660
aaagtacaat atgagagcag tgagcctgca gattttaagg tggatgaaga tggcatggtg     720
tatgccgtga aagctttcc actctcttct gagcatgcca agttcctgat atatgcccaa     780
gacaaagaga cccaggaaaa gtggcaagtg gcagtaaaat tgagcctgaa gccaaccta     840 actgaggagt cagtgaagga gtcagcagaa gttgaagaaa tagtgttccc aagacaattc     900
agtaagcaca gtggccacct acaaaggcag aagagagact gggtcatccc tccaatcaac     960
ttgccagaaa actccagggg acctttcct caagagcttg tcaggatcag gtctgataga    1020 gataaaaaccc tttcactgcg gtacagtgta actgggccag gagctgacca gcctccaact    1080
ggtatcttca ttatcaaccc catctcgggt cagctgtcgg tgacaaagcc cctggatcgc    1140
gagcagatag cccggtttca tttgagggca catgcagtag atattaatgg aaatcaagtg    1200
gagaacccca ttgacattgt catcaatgtt attgacatga atgacaacag acctgagttc    1260
ttacaccagg tttggaatgg acagttcct gagggatcaa agcctggaac atatgtgatg    1320
accgtaacag caattgatgc tgacgatccc aatgccctca tgggatgtt gaggtacaga    1380 atcgtgtctc aggctccaag cacccccttca cccaacatgt ttacaatcaa caatgagact    1440
ggtgacatca tcacagtggc agctggactt gatcgagaaa agtgcaaca gtatacgtta    1500 ataattcaag ctacagacat ggaaggcaat cccacatatg gcctttcaaa cacagccacg    1560
gccgtcatca cagtgacaga tgtcaatgac aatcctccag agtttactgc catgacgttt    1620
tatggtgaag ttcctgagaa cagggtagac atcatagtag ctaatctaac tgtgaccgat    1680
```

```
aaggatcaac cccatacacc agcctggaac gcagtgtaca gaatcagtgg cggagatcct    1740
actggacggt tcgccatcca gaccgaccca aacagcaacg acgggttagt caccgtggtc    1800
aaaccaatcg actttgaaac aaataggatg tttgtcctta ctgttgctgc agaaaatcaa    1860
gtgccattag ccaagggaat tcagcacccg cctcagtcaa ctgcaaccgt gtctgttaca    1920
gttattgacg taaatgaaaa cccttatttt gcccccaatc ctaagatcat tcgccaagaa    1980
gaagggcttc atgccggtac catgttgaca acattcactg ctcaggaccc agatcgatat    2040
atgcagcaaa atattagata cactaaatta tctgatcctg ccaattggct aaaaatagat    2100
cctgtgaatg acaaataac tacaattgct gttttggacc gagaatcacc aaatgtgaaa    2160
aacaatatat ataatgctac tttccttgct tctgacaatg aattcctcc tatgagtgga    2220
acaggaacgc tgcagatcta tttacttgat attaatgaca atgcccctca agtgttacct    2280
caagaggcag agacttgcga aactccagac cccaattcaa ttaatattac agcacttgat    2340
tatgacattg atccaaatgc tggaccattt gcttttgatc ttcctttatc tccagtgact    2400
attaagagaa attggaccat cactcggctt aatggtgatt ttgctcagct taatttaaag    2460
ataaaatttc ttgaagctgg tatctatgaa gttcccatca taatcacaga ttcgggtaat    2520
cctcccaaat caaatatttc catcctgcgc gtgaaggttt gccagtgtga ctccaacggg    2580
gactgcacag atgtggacag gattgtgggt gcggggcttg gcaccggtgc catcattgcc    2640
atcctgctct gcatcatcat cctgcttatc cttgtgctga tgtttgtggt atggatgaaa    2700
cgccgggata agaacgcca ggccaaacaa cttttaattg atccagaaga tgatgtaaga    2760
gataatattt taaatatga tgaagaaggt ggaggagaag aagaccagga ctatgacttg    2820
agccagctgc agcagcctga cactgtggag cctgatgcca tcaagcctgt gggaatccga    2880
cgaatggatg aaagacccat ccacgccgag ccccagtatc cggtccgatc tgcagcccca    2940
caccctggag acattgggga cttcattaat gagggcctta agcggctga caatgacccc    3000
acagctccac catatgactc cctgttagtg tttgactatg aaggcagtgg ctccactgct    3060
gggtccttga gctcccttaa ttcctcaagt agtggtggtg agcaggacta tgattacctg    3120
aacgactggg ggccacggtt caagaaactt gctgacatgt atggtggagg tgatgactga    3180
acttcagggt gaacttggtt tttggacaag tacaaacaat ttcaactgat attcccaaaa    3240
agcattcaga agctaggctt taactttgta gtctactagc acagtgcttg ctggaggctt    3300
tggcataggc tgcaaaccaa tttgggctca gagggaatat cagtgatcca tactgtttgg    3360
aaaaacactg agctcagtta cacttgaatt ttacagtaca gaagcactgg gattttatgt    3420
gcctttttgt acctttttca gattggaatt agttttctgt ttaaggcttt aatggtactg    3480
atttctgaaa cgataagtaa aagacaaaat attttgtggt gggagcagta agttaaacca    3540
tgatatgctt caacacgctt tgttacatt gcatttgctt ttattaaaat acaaaattaa    3600
acaaacaaaa aaactcatgg agcgatttta ttatcttggg ggatgagacc atgagattgg    3660
aaaatgtaca ttacttctag ttttagactt tagtttgttt tttttttttt cactaaaatc    3720
ttaaaactta ctcagctggt tgcaaataaa gggagttttc atatcaccaa tttgtagcaa    3780
aattgaattt tttcataaac tagaatgtta gacacatttt ggtcttaatc catgtacact    3840
tttttatttc tgtattttt cacttcactg taaaaatagt atgtgtacat aatgtttat     3900
tggcatagtc tatggagaag tgcagaaaact tcagaacatg tgtatgtatt atttggacta    3960
tggattcagg ttttttgcat gtttatatct ttcgttatgg ataaagtatt tacaaaacag    4020
tgacatttga ttcaattgtt gagctgtagt tagaatactc aatttttaat tttttaatt     4080
```

-continued

```
tttttatttt ttattttctt tttggtttgg ggagggagaa aagttcttag cacaaatgtt    4140
ttacataatt tgtaccaaaa aaaaaaaaaa aggaaaggaa agaaaggggt ggcctgacac    4200
tggtggcact actaagtgtg tgtttttta aaaaaaaat ggaaaaaaaa aagcttttaa     4260
actggagaga cttctgacaa cagctttgcc tctgtattgt gtaccagaat ataaatgata    4320
cacctctgac cccagcgttc tgaataaaat gctaattttg gatctggaaa aaaaaaaaa     4380
```

<210> SEQ ID NO 6
<211> LENGTH: 906
<212> TYPE: PRT
<213> ORGANISM: human

<400> SEQUENCE: 6

```
Met Cys Arg Ile Ala Gly Ala Leu Arg Thr Leu Leu Pro Leu Leu Ala
1               5                   10                  15

Ala Leu Gln Ala Ser Val Glu Ala Ser Gly Glu Ile Ala Leu Cys
            20                  25                  30

Lys Thr Gly Phe Pro Glu Asp Val Tyr Ser Ala Val Leu Ser Lys Asp
        35                  40                  45

Val His Glu Gly Gln Pro Leu Leu Asn Val Lys Phe Ser Asn Cys Asn
    50                  55                  60

Gly Lys Arg Lys Val Gln Tyr Glu Ser Ser Glu Pro Ala Asp Phe Lys
65                  70                  75                  80

Val Asp Glu Asp Gly Met Val Tyr Ala Val Arg Ser Phe Pro Leu Ser
                85                  90                  95

Ser Glu His Ala Lys Phe Leu Ile Tyr Ala Gln Asp Lys Glu Thr Gln
            100                 105                 110

Glu Lys Trp Gln Val Ala Val Lys Leu Ser Leu Lys Pro Thr Leu Thr
        115                 120                 125

Glu Glu Ser Val Lys Glu Ser Ala Glu Val Glu Glu Ile Val Phe Pro
    130                 135                 140

Arg Gln Phe Ser Lys His Ser Gly His Leu Gln Arg Gln Lys Arg Asp
145                 150                 155                 160

Trp Val Ile Pro Pro Ile Asn Leu Pro Glu Asn Ser Arg Gly Pro Phe
                165                 170                 175

Pro Gln Glu Leu Val Arg Ile Arg Ser Asp Arg Asp Lys Asn Leu Ser
            180                 185                 190

Leu Arg Tyr Ser Val Thr Gly Pro Gly Ala Asp Gln Pro Pro Thr Gly
        195                 200                 205

Ile Phe Ile Ile Asn Pro Ile Ser Gly Gln Leu Ser Val Thr Lys Pro
    210                 215                 220

Leu Asp Arg Glu Gln Ile Ala Arg Phe His Leu Arg Ala His Ala Val
225                 230                 235                 240

Asp Ile Asn Gly Asn Gln Val Glu Asn Pro Ile Asp Ile Val Ile Asn
                245                 250                 255

Val Ile Asp Met Asn Asp Asn Arg Pro Glu Phe Leu His Gln Val Trp
            260                 265                 270

Asn Gly Thr Val Pro Glu Gly Ser Lys Pro Gly Thr Tyr Val Met Thr
        275                 280                 285

Val Thr Ala Ile Asp Ala Asp Asp Pro Asn Ala Leu Asn Gly Met Leu
    290                 295                 300

Arg Tyr Arg Ile Val Ser Gln Ala Pro Ser Thr Pro Ser Pro Asn Met
305                 310                 315                 320
```

```
Phe Thr Ile Asn Asn Glu Thr Gly Asp Ile Ile Val Ala Ala Gly
                325                 330                 335

Leu Asp Arg Glu Lys Val Gln Gln Tyr Thr Leu Ile Ile Gln Ala Thr
            340                 345                 350

Asp Met Glu Gly Asn Pro Thr Tyr Gly Leu Ser Asn Thr Ala Thr Ala
        355                 360                 365

Val Ile Thr Val Thr Asp Val Asn Asp Asn Pro Pro Glu Phe Thr Ala
    370                 375                 380

Met Thr Phe Tyr Gly Glu Val Pro Glu Asn Arg Val Asp Ile Ile Val
385                 390                 395                 400

Ala Asn Leu Thr Val Thr Asp Lys Asp Gln Pro His Thr Pro Ala Trp
            405                 410                 415

Asn Ala Val Tyr Arg Ile Ser Gly Gly Asp Pro Thr Gly Arg Phe Ala
        420                 425                 430

Ile Gln Thr Asp Pro Asn Ser Asn Asp Gly Leu Val Thr Val Val Lys
    435                 440                 445

Pro Ile Asp Phe Glu Thr Asn Arg Met Phe Val Leu Thr Val Ala Ala
450                 455                 460

Glu Asn Gln Val Pro Leu Ala Lys Gly Ile Gln His Pro Pro Gln Ser
465                 470                 475                 480

Thr Ala Thr Val Ser Val Thr Val Ile Asp Val Asn Glu Asn Pro Tyr
            485                 490                 495

Phe Ala Pro Asn Pro Lys Ile Ile Arg Gln Glu Gly Leu His Ala
        500                 505                 510

Gly Thr Met Leu Thr Thr Phe Thr Ala Gln Asp Pro Asp Arg Tyr Met
    515                 520                 525

Gln Gln Asn Ile Arg Tyr Thr Lys Leu Ser Asp Pro Ala Asn Trp Leu
530                 535                 540

Lys Ile Asp Pro Val Asn Gly Gln Ile Thr Thr Ile Ala Val Leu Asp
545                 550                 555                 560

Arg Glu Ser Pro Asn Val Lys Asn Asn Ile Tyr Asn Ala Thr Phe Leu
            565                 570                 575

Ala Ser Asp Asn Gly Ile Pro Pro Met Ser Gly Thr Gly Thr Leu Gln
        580                 585                 590

Ile Tyr Leu Leu Asp Ile Asn Asp Asn Ala Pro Gln Val Leu Pro Gln
    595                 600                 605

Glu Ala Glu Thr Cys Glu Thr Pro Asp Pro Asn Ser Ile Asn Ile Thr
610                 615                 620

Ala Leu Asp Tyr Asp Ile Asp Pro Asn Ala Gly Pro Phe Ala Phe Asp
625                 630                 635                 640

Leu Pro Leu Ser Pro Val Thr Ile Lys Arg Asn Trp Thr Ile Thr Arg
            645                 650                 655

Leu Asn Gly Asp Phe Ala Gln Leu Asn Leu Lys Ile Lys Phe Leu Glu
        660                 665                 670

Ala Gly Ile Tyr Glu Val Pro Ile Ile Ile Thr Asp Ser Gly Asn Pro
    675                 680                 685

Pro Lys Ser Asn Ile Ser Ile Leu Arg Val Lys Val Cys Gln Cys Asp
690                 695                 700

Ser Asn Gly Asp Cys Thr Asp Val Asp Arg Ile Val Gly Ala Gly Leu
705                 710                 715                 720

Gly Thr Gly Ala Ile Ile Ala Ile Leu Leu Cys Ile Ile Ile Leu Leu
            725                 730                 735

Ile Leu Val Leu Met Phe Val Val Trp Met Lys Arg Arg Asp Lys Glu
```

```
                    740                 745                 750
Arg Gln Ala Lys Gln Leu Leu Ile Asp Pro Glu Asp Val Arg Asp
            755                 760                 765
Asn Ile Leu Lys Tyr Asp Glu Glu Gly Gly Gly Glu Asp Gln Asp
            770                 775                 780
Tyr Asp Leu Ser Gln Leu Gln Gln Pro Asp Thr Val Glu Pro Asp Ala
785                 790                 795                 800
Ile Lys Pro Val Gly Ile Arg Arg Met Asp Glu Arg Pro Ile His Ala
            805                 810                 815
Glu Pro Gln Tyr Pro Val Arg Ser Ala Ala Pro His Pro Gly Asp Ile
            820                 825                 830
Gly Asp Phe Ile Asn Glu Gly Leu Lys Ala Ala Asp Asn Asp Pro Thr
            835                 840                 845
Ala Pro Pro Tyr Asp Ser Leu Leu Val Phe Asp Tyr Glu Gly Ser Gly
            850                 855                 860
Ser Thr Ala Gly Ser Leu Ser Ser Leu Asn Ser Ser Ser Ser Gly Gly
865                 870                 875                 880
Glu Gln Asp Tyr Asp Tyr Leu Asn Asp Trp Gly Pro Arg Phe Lys Lys
            885                 890                 895
Leu Ala Asp Met Tyr Gly Gly Gly Asp Asp
            900                 905
```

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic DNA

<400> SEQUENCE: 7
cgcggtacca tggggctccc tcgt                                            24

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic DNA

<400> SEQUENCE: 8
ccgtctagat aacctcsctt ccagggtcc                                       29

<210> SEQ ID NO 9
<211> LENGTH: 41
<212> TYPE: DNA
<213> ORGANISM: Artificial Sequence
<220> FEATURE:
<223> OTHER INFORMATION: Description of Artificial Sequence: Synthetic DNA

<400> SEQUENCE: 9
tatggagctc ggtaccgatt gggtggttgc tccaatatct g                         41

<210> SEQ ID NO 10
<211> LENGTH: 44
<212> TYPE: DNA
<213> ORGANISM: Artificial Sequence
<220> FEATURE:
<223> OTHER INFORMATION: Description of Artificial Sequence: Synthetic DNA

<400> SEQUENCE: 10
agattaccta tctagactac tgcatcacag aagtacctgg tagg                    44

<210> SEQ ID NO 11
<211> LENGTH: 43
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 11
tatggagctc ggtaccaagt ctaataaaga tagagacacc aag                     43

<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 12
agattaccta tctagactac ctctgcacct catggcccac tgcattctca              50

<210> SEQ ID NO 13
<211> LENGTH: 41
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 13
tatggagctc ggtaccgtga cagccacgga tgaggatgat g                       41

<210> SEQ ID NO 14
<211> LENGTH: 41
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 14
agattaccta tctagactag acacacacag gctccccagt g                       41

<210> SEQ ID NO 15
<211> LENGTH: 38
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 15
tatggagctc ggtaccctga cggtcactga tctggacg                           38

<210> SEQ ID NO 16
<211> LENGTH: 47
<212> TYPE: DNA
<213> ORGANISM: Artificial Sequence
<220> FEATURE:
<223> OTHER INFORMATION: Description of Artificial Sequence: Synthetic
      DNA

```
<400> SEQUENCE: 16
agattaccta tctagactag ggctcaggga ctgggccatg gtcattg         47

<210> SEQ ID NO 17
<211> LENGTH: 41
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 17
tatggagctc ggtacctaca ctgcagaaga ccctgacaag g               41

<210> SEQ ID NO 18
<211> LENGTH: 50
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 18
agattaccta tctagactaa cctcccttcc agggtccagg gcaggtttcg       50

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 19
gayatccagc tgactcagcc                                       20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 20
gayattgttc tcwcccagtc                                       20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 21
gayattgtgm tmactcagtc                                       20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 22
```
gayattgtgy tracacagtc                                          20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 23
gayattgtra tgacmcagtc                                          20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 24
gayattmaga tramccagtc                                          20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 25
gayattcaga tgaydcagtc                                          20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 26
gayatycaga tgacacagac                                          20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 27
gayattgttc tcawccagtc                                          20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 28
gayattgwgc tsacccaatc                                                20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 29
gayattstra tgacccartc                                                20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 30
gayrttktga tgacccarac                                                20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 31
gayattgtga tgacbcagkc                                                20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 32
gayattgtga taacycagga                                                20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 33
gayattgtga tgacccagwt                                                20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 34
gayattgtga tgacacaacc                                                20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 35
gayattttgc tgactcagtc                                                    20

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic DNA

<400> SEQUENCE: 36
ggsaccaarc tggaaatmaa a                                                  21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic DNA

<400> SEQUENCE: 37
gggacaaagt tggaaataaa a                                                  21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic DNA

<400> SEQUENCE: 38
gggaccaagc tggagctgaa a                                                  21

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic DNA

<400> SEQUENCE: 39
atgragwcac akwcycaggt cttt                                               24

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic DNA

<400> SEQUENCE: 40
atggagacag acacactcct gctat                                              25

<210> SEQ ID NO 41
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 41
atggagwcag acacactsct gytatgggt                                              29

<210> SEQ ID NO 42
<211> LENGTH: 32
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (27)..(27)
<223> OTHER INFORMATION: n is inosine

<400> SEQUENCE: 42
atgaggrccc ctgctcagwt tyttggnwtc tt                                          32

<210> SEQ ID NO 43
<211> LENGTH: 31
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 43
atgggcwtca agatgragtc acakwyycwg g                                           31

<210> SEQ ID NO 44
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 44
atgagtgtgc ycactcaggt cctggsgtt                                              29

<210> SEQ ID NO 45
<211> LENGTH: 31
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 45
atgtggggay cgktttyamm cttttcaatt g                                           31

<210> SEQ ID NO 46
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 46
atggaagccc cagctcagct tctcttcc					28

<210> SEQ ID NO 47
<211> LENGTH: 26
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (1)..(26)
<223> OTHER INFORMATION: any "n" is inosine

<400> SEQUENCE: 47
atgagnmmkt cnmttcantt cytggg					26

<210> SEQ ID NO 48
<211> LENGTH: 26
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (1)..(26)
<223> OTHER INFORMATION: any "n" is inosine

<400> SEQUENCE: 48
atgakgthcy cngctcagyt yctnrg					26

<210> SEQ ID NO 49
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 49
atggtrtccw casctcagtt ccttg					25

<210> SEQ ID NO 50
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 50
atgtatatat gtttgttgtc tatttct					27

<210> SEQ ID NO 51
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 51
atgaagttgc ctgttaggct gttggtgct					29

<210> SEQ ID NO 52
<211> LENGTH: 29
<212> TYPE: DNA
<213> ORGANISM: Artificial Sequence
<220> FEATURE:

<223> OTHER INFORMATION: Description of Artificial Sequence: Synthetic
      DNA

<400> SEQUENCE: 52
atggatttwc argtgcagat twtcagctt                                                29

<210> SEQ ID NO 53
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 53
atggtyctya tvtccttgct gttctgg                                                  27

<210> SEQ ID NO 54
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 54
atggtyctya tvttrctgct gctatgg                                                  27

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 55
actggatggt gggaagatgg a                                                        21

<210> SEQ ID NO 56
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 56
atggratgsa gctgkgtmat sctctt                                                   26

<210> SEQ ID NO 57
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 57
atgracttcg ggytgagctk ggtttt                                                   26

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: Synthetic

```
    DNA

<400> SEQUENCE: 58
atggctgtct tggggctgct cttct                                              25

<210> SEQ ID NO 59
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 59
atggrcagrc ttacwtyy                                                      18

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 60
saggtsmarc tksagsagtc wgg                                                23

<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 61
casccccatc dgtctatcc                                                     19
```

US 9,328,160 B2

ANTI-CDH3 ANTIBODY HAVING HIGH INTERNALIZATION CAPACITY

TECHNICAL FIELD

The present invention relates to an anti-cadherin antibody that recognizes a certain cadherin domain and has a high internalization capacity. Further, the present invention relates to an anti-cadherin antibody-drug conjugate. Furthermore, the present invention relates to a method for the use of an anti-cadherin antibody-drug conjugate.

BACKGROUND ART

Cancer is a serious disease, which is one of the leading causes of death, but the need for treatment thereof has not yet been satisfied. In order to solve the problem of conventional chemotherapy techniques, which disadvantageously damage normal cells, in recent years, active studies have been conducted on a cancer treatment technique performed with the use of a molecular-targeting drug that has been designed to target a specific molecule expressed specifically in a cancer cell.

An example of a molecule that can be the target of a molecular-targeted drug in cancer is cadherin. Cadherin is a membrane protein which was discovered as a molecule associated with calcium-dependent, homophilic cell adhesion (Non-Patent Document 1). Proteins having cadherin repeats (ECs) composed of about 110 amino acid residues, which are highly homologous to each other, are referred to as the cadherin superfamily. The cadherin superfamily includes 120 or more protein species and plays a key role in maintenance of the multicell-layered structure.

It has been reported that cadherin expression levels are elevated in cancer cells. Accordingly, use of a drug comprising an antibody that recognizes cadherin and an anticancer agent bound thereto or an antibody having antibody-dependent cytotoxic activity (ADCC) for treatment of cancer has been studied for cancer cells exhibiting a higher cadherin expression level in cancer tissue compared with that in normal tissue (Patent Document 1: Patent Document 2).

Proteins belonging to the cadherin superfamily can be roughly classified as follows in accordance with the structural features thereof: 1) classical cadherins; 2) desmosomal cadherins; 3) protocadherins; and 4) others. Major members of the cadherin superfamily; i.e., classical cadherins such as E-cadherin (CDH1), N-cadherin (CDH2), and P-cadherin (CDH3) are highly homologous to each other (FIG. 1). Specifically, such proteins are single-pass transmembrane proteins that are presumed to form dimers, and have 5 cadherin extracellular domains (EC1 to EC5) and intracellular domains. Cell adhesion mediated by classical cadherins are characterized by adhesion between homogeneous cells, and such cell adhesion takes place when the cells recognizes the cadherin molecule of the same species that are expressed specifically and differently depending on cell species. Specifically, CDH1 recognizes and binds to CDH1, and CDH3 recognizes and binds to CDH3. Thus, cells of the same species adhere to each other (FIG. 2).

Homologous/heterologous cadherins are deduced to be recognized by the cadherin domain 1 (EC1) located at the N terminus of the extracellular domain (Non-Patent Document 2). Klingel et al. demonstrate that, even when a sequence comprising positions 1 to 213 of the amino acid sequence of human CDH3 (SEQ ID NO: 2) is substituted with the corresponding domain of human CDH1, it would bind to CDH3 instead of CDH1 (Non-Patent Document 3). Thus, classical cadherins, including CDH1 and CDH3, are considered to bind each other based on the same mechanism.

In recent years, many antibody drugs for cancer treatment have actually been marketed as molecular-targeted drugs, and many of such drugs are based on the ADCC mechanism. However, the drug efficacy thereof is not always sufficient, and development of techniques exerting more potent antitumor effects has been attempted.

An example of an effective means for potentiating the antitumor activity of the antibody is a conjugate of an antibody and a highly toxic drug (toxin). If a toxin is administered to a patient by itself, disadvantageously, it damages normal tissues. Accordingly, it cannot serve as an effective therapeutic means. By binding a toxin to an antibody that binds to a tumor-cell-specific antigen, however, a toxin can selectively destroy tumor cells without adversely affecting normal tissue. Such drugs are referred to as "antibody-drug conjugates (ADCs)." Specifically, a toxin does not exert its toxicity while being bound to an antibody. However, some antibodies are incorporated into cells when the antibodys are bound to an target antigen, and are then degraded in lysosomes. Accordingly, such antibodies comprising toxins bound thereto are incorporated and degraded in cells, toxins are released, toxicity is expressed selectively in specific cells, and cells are destroyed thereby.

In ADCs, drugs bound to antibodies circulate in the blood, and such drugs accumulate and exert drug efficacy in target tumor cells. It is not preferable that a drug be released at any site other than tumor regions (i.e., liberation from antibodies) due to a risk of adverse side effects. That is, it is preferable that ADCs be designed in such a manner that drugs bound to antibodies are first incorporated into cells and then liberated from the antibodies. From such point of view, Genentech Inc. have developed drugs comprising Trastuzumab and toxin bound thereto (T-DM1), the developed drugs have been subjected to clinical testing, and such drugs exert remarkably high clinical effects. That is, it is not sufficient if ADCs merely accumulate in target cancer cells, and it is necessary that ADCs are efficiently incorporated into cancer cells. Such capacity (an internalization capacity of an antibody) is closely related to drug efficacy of ADC.

The internalization capacity of an antibody is affected by both a membrane surface protein to which an antibody binds and an antibody itself. Accordingly, such capacity cannot be unambiguously deduced based on molecular structure, physical properties of antibody, or other factors. Screening of relevant antibodies with a high internalization capacity against antigens is accordingly a big object in the development of ADCs. The present invention is intended to overcome such object with respect to the CDH3 antigen.

As described above, the concept of cancer treatment with the use of ADCs has been known. However, none of such techniques suggest the efficacy of an immunocomplex resulting from conjugation of an anti-cadherin antibody having a high internalization capacity with a drug. While the correlation between a domain structure and a cadherin function has been reported, no reports have been made regarding the correlation between a domain structure and an internalization capacity.

PRIOR ART DOCUMENTS

Patent Documents

Patent Document 1: WO 2002/097395
Patent Document 2: WO 2007/102525

Non-Patent Documents

Non-Patent Document 1: Yoshida and Takeichi, Cell 28: 217-224, 1982
Non-Patent Document 2: Nose, A. et al., Cell 61; 147-155, 1990
Non-Patent Document 3: Klingel, H. et al., Journal of Cell Science 113: 2829-36, 2000

SUMMARY OF THE INVENTION

Objects to Be Solved by the Invention

It is an object of the present invention to provide an anti-cadherin antibody having a high internalization capacity. It is another object of the present invention to provide an anti-cadherin antibody-drug conjugate that effectively kills cadherin-expressing cancer cells with the use of such antibody.

Means for Solving the Objects

The present inventors have conducted concentrated studies in order to solve the above objects. They assayed the internalization capacity of the anti-human CDH3 antibody and discovered that each antibody would exert different internalization capacity. Thus, they classified antibodies depending on domains recognized thereby and discovered that antibodies with a high internalization capacity would be highly likely to recognize the cadherin domain 1 (EC 1).

Examples of factors that define the internalization capacity of the antibody include affinity of an antibody for an antigen and an epitope recognized by an antibody, although the details thereof remain unknown. The present invention has been completed by performing screening while focusing especially on the correlation between an antibody and an epitope recognized thereby.

According to the present invention, the followings are provided.

(1) An anti-cadherin antibody which recognizes a cadherin domain 1 (EC1) of cadherin and exhibits a high internalization capacity.
(2) The antibody according to (1), wherein the cadherin is P-cadherin.
(3) The antibody according to (1) or (2), which is produced by an antibody-producing cell obtained from an immunized animal into which P-cadherin or a P-cadherin-expressing cell has been administered as an immunogen.
(4) The antibody according to (3), wherein the P-cadherin is a full-length cadherin, a soluble P-cadherin obtained by expression of only the extracellular domain only, or a fragment thereof.
(5) The antibody according to any one of (1) to (4), which is a monoclonal antibody.
(6) The antibody according to (5), wherein the monoclonal antibody is a chimeric antibody, humanized antibody, or human antibody.
(7) A monoclonal antibody which is produced by a cell deposited under Accession Number NITE BP-988, NITE BP-1145, NITE BP-1147, or NITE BP-1148.
(8) A chimeric or humanized antibody which is prepared by modification of the monoclonal antibody according to (7).
(9) An antibody which has a VH and/or VL domain comprising an amino acid sequence having 90% or higher sequence identity with respect to the amino acid sequence of the VH and/or VL domain of the monoclonal antibody according to (7), or a fragment thereof.
(10) The antibody according to any one of (1) to (9), wherein the antibody is an antibody fragment which is selected from the group consisting of Fab, Fab', F(ab')$_2$, a single chain antibody (scFv), a dimeric V region (Diabody), a disulfide-stabilized V region (dsFv), and a peptide comprising CDR.
(11) A cell line which produces the antibody of any one of (5) to (10).
(12) A cell line which is deposited under Accession Number NITE BP-988, NITE BP-1145, NITE BP-1147, or NITE BP-1148.
(13) A cytotoxic agent which comprises the antibody of any one of (1) to (10).
(14) The cytotoxic agent according to (13), wherein a cytotoxic substance is conjugated to the antibody.
(15) The cytotoxic agent according to (14), wherein the cytotoxic substance is a drug, toxin, or radioactive substance.
(16) The cytotoxic agent according to (15), wherein the cytotoxic substance is a drug which is selected from maytansinoid or derivative thereof, or auristatin or derivative thereof.
(17) The cytotoxic agent according to (16), wherein the cytotoxic substance is a maytansinoid derivative selected from DM1, DM3 or DM4 or an auristatin derivative selected from MMAE or MMAF.
(18) The cytotoxic agent according to any one of (14) to (17), wherein the antibody is conjugated to a cytotoxic substance via a linker.
(19) The cytotoxic agent according to (18), wherein the linker is a bifunctional cross-linking agent.
(20) The cytotoxic agent according to (18) or (19), wherein the linker is selected from the group consisting of: sulfosuccinimidyl-4-(N-maleimidomethyl)cyclohexane-1-carboxylate (Sulfo-SMCC), N-succinimidyl-4-(maleimidomethyl) cyclohexanecarboxylate (SMCC), N-succinimidyl-4-(N-maleimidomethyl)-cyclohexane-1-carboxy-(6-amidocaproate) (LC-SMCC), rc-maleimidoundecanoic acid N-succinimidyl ester (KMUA), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl-6-(β-maleimidopropionamido)hexanoate (SMPH), N-succinimidyl-4-(p-maleimidophenyl)-butyrate (SMPB), N-(p-maleimidophenyl)isocyanate (PMPI), 6-maleimidocaproyl (MC), maleimidopropanoyl (MP), p-aminobenzyloxycarbonyl (PAB), N-succinimidyl-4-(2-pyridylthio)pentanoate (SPP), N-succinimidyl(4-iodoacetyl)aminobenzoate (STAB), valine-citrulline (val-cit), and alanine-phenylalanine (ala-phe).
(21) The cytotoxic agent according to (19) or (20), wherein 1 to 10 DM1 molecules are conjugated to a single antibody molecule via a linker.
(22) A pharmaceutical composition which comprises, as an active ingredient, the cytotoxic agent according to any one of (13) to (21).
(23) A therapeutic agent for disease with a highly expressed human CDH3, which comprises, as an active ingredient, the cytotoxic agent of any one of (13) to (21).
(24) The therapeutic agent according to (23), wherein the disease with a highly expressed human CDH3 is cancer.

The present invention further provides a method for killing cells which highly express cadherin in a patient which comprises administering the antibody or the cytotoxic agent of the present invention to a patient with a high expression of cadherin. Further, the present invention provides a method for treatment of disease with a high expression of cadherin, which comprises administering the antibody or the cytotoxic agent of the present invention to a patient with a high expression of cadherin.

Further, the present invention provides the use of the antibody of the present invention for the production of a cytotoxic agent. Further, the present invention provides the use of the antibody of the present invention for the production of a therapeutic agent for diseases with a high expression of cadherin.

Effects of the Invention

The anti-cadherin antibody of the present invention recognizes the cadherin domain 1 (EC1) of cadherin and has a high internalization capacity. An antibody capable of exerting a high internalization capacity is useful for the preparation of a modified or engineered antibody. For example, a drug which exerts toxicity in a cell is linked to the anti-cadherin antibody of the present invention, and the resultant is administered to a patient having cancer cells which expresses cadherin. Thus, potent anti-tumor effects can be expected. Specifically, the anti-cadherin antibody of the present invention is useful as an anticancer agent. According to the present invention, an immunocomplex comprising the antibody and a chemotherapeutic agent linked thereto via a linker is provided. This immunocomplex exhibits more potent cytotoxicity on cadherin-expressing cancer cell lines, compared with an antibody to which no chemotherapeutic agent has been linked. Accordingly, potent anti-tumor effects can be expected for the administration of the immunocomplex to a patient having cadherin-expressing cancer cells. Specifically, the immunocomplex of the present invention is useful as an anticancer agent.

BRIEF DESCRIPTION OF THE DRAWINGS

FIG. 1 shows sequences of maturation proteins of CDH1 (E-cadherin)(positions 155 to 882 of SEQ ID NO: 3), CDH2 (N-cadherin)(positions 160 to 906 of SEQ ID NO: 6), and CDH3 (P-cadherin) (positions 108 to 829 of SEQ ID NO: 2) from which signal and propeptide sequences have been removed.

FIG. 7 shows the internalization capacity of the anti-human CDH3 mouse antibody and the viability of human CDH3 expressing cells to which various types of antibodies and the saporin-labeled anti-mouse IgG antibody have been administered (relative to the cell viability (100%) attained without the addition of antibodies). Assays were carried out multiple times by changing types of antibodies administered (A and B).

FIG. 11 shows the results of epitope analysis of PPAT-055-13 using a peptide array. A numerical value on the X axis indicates the number of a peptide on a peptide array (A: PPAT-055-13; B: in the absence of primary antibody).

EMBODIMENTS FOR CARRYING OUT THE INVENTION

Figure 2:
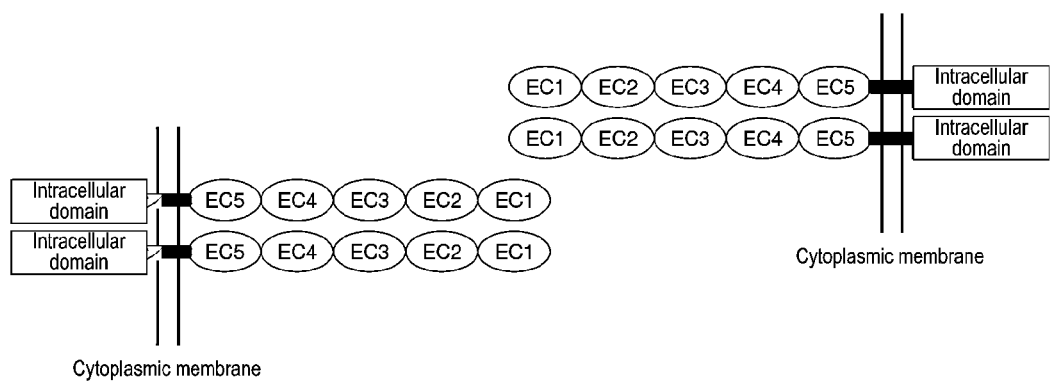
FIG. 2 shows the adhesion mechanism of molecules belonging to the classical cadherin family.

Hereafter, the present invention is described in greater detail.

The antibody of the present invention is an anti-cadherin antibody which recognizes the cadherin domain 1 (EC1) of cadherin and has a high internalization capacity.

In this description, the cadherin domain 1 (EC1), the cadherin domain 2 (EC2), the cadherin domain 3 (EC3), the cadherin domain 4 (EC4), and the cadherin domain 5 (EC5) of P-cadherin (CDH3), E-cadherin (CDH1) and N-cadherin (CDH2) each represent domains described below. The corresponding domains of other cadherins can be determined by comparing known cadherin protein sequences obtained from Genbank or other institutions. Sequence comparison can be carried out using a known program, such as ClustalW2 (Thompson, J. D. et al., Nucleic Acids Research 22 (22): 3673-3680, 1994) or ClustalX2 (Thompson, J. D. et al., Nucleic Acids Research 25 (24): 4876-4882, 1997).

P-cadherin (CDH3)
Cadherin domain 1 (EC1): positions 108 to 236 of the amino acid sequence as shown in SEQ ID NO: 2
Cadherin domain 2 (EC2): positions 237 to 348 of the amino acid sequence as shown in SEQ ID NO: 2
Cadherin domain 3 (EC3): positions 349 to 461 of the amino acid sequence as shown in SEQ ID NO: 2
Cadherin domain 4 (EC4): positions 462 to 550 of the amino acid sequence as shown in SEQ ID NO: 2
Cadherin domain 5 (EC5): positions 551 to 654 of the amino acid sequence as shown in SEQ ID NO: 2
E-cadherin (CDH1)

Cadherin domain 1 (EC1): positions 155 to 283 of the amino acid sequence as shown in SEQ ID NO: 4
Cadherin domain 2 (EC2): positions 284 to 395 of the amino acid sequence as shown in SEQ ID NO: 4
Cadherin domain 3 (EC3): positions 396 to 507 of the amino acid sequence as shown in SEQ ID NO: 4
Cadherin domain 4 (EC4): positions 508 to 597 of the amino acid sequence as shown in SEQ ID NO: 4
Cadherin domain 5 (EC5): positions 598 to 704 of the amino acid sequence as shown in SEQ ID NO: 4
N-cadherin (CDH2)
Cadherin domain 1 (EC1): positions 160 to 288 of the amino acid sequence as shown in SEQ ID NO: 6
Cadherin domain 2 (EC2): positions 289 to 402 of the amino acid sequence as shown in SEQ ID NO: 6
Cadherin domain 3 (EC3): positions 403 to 518 of the amino acid sequence as shown in SEQ ID NO: 6
Cadherin domain 4 (EC4): positions 519 to 607 of the amino acid sequence as shown in SEQ ID NO: 6
Cadherin domain 5 (EC5): positions 608 to 719 of the amino acid sequence as shown in SEQ ID NO: 6

The internalization capacity of the antibody can be assayed in accordance with a known technique. For example, a method comprising labeling an antibody (or a secondary antibody) with RI, a fluorescent dye, or other substance and assaying the level of label incorporation (RI and fluorescence intensity) and a method for assaying cell death using a toxin such as saporin (e.g., a saporin-labeled anti-mouse IgG antibody) are known. From the viewpoint of sensitivity and convenience, a method involving the use of an antibody labeled with a saporin toxin is superior to other techniques. Numerical values indicating the degrees of internalization capacity used herein are determined under the conditions as described in Example 6 or 15. Specifically, the internalization capacity is assayed in the following manner.

(1) Assay of Internalization Capacity

The anti-human CDH3 antibody (100 ng) and the saporin-labeled antibody (100 ng, Advanced Targeting Systems, Inc.) were added to the human CDH3 expressing cells, and the resultants were heated in an incubator at 37° C. in the presence of 5% $CO_2$ for 3 days. Thereafter, activity of an antibody for cell destruction was evaluated using a viable cell counting reagent (Cell Counting Kit-8, DOJINDO LABORATORIES, Inc.). Cell destruction activity was expressed relative to 100% cell viability attained without the addition of antibody.

In the present invention, "high internalization capacity" refers to that the viability of CDH3 expressing cells to which the antibody of interest and the saporin-labeled anti-mouse IgG antibody have been administered (represented relative to 100% cell viability attained without the addition of antibody), is preferably 70% or less, more preferably 60% or less, more preferably 50% or less, more preferably 45% or less, further preferably 40% or less, and particularly preferably 35% or less.

It is preferable that the antibody of the present invention recognize a classical cadherin. Examples thereof include, but are not limited to, E-cadherin, N-cadherin, and P-cadherin.

As an antigen used for the preparation of the antibody of the present invention, cadherin or a partial peptide thereof can be used. An example thereof is, but is not limited to, a soluble CDH3 protein.

The antibody of the present invention may be a polyclonal or monoclonal antibody. The (polyclonal or monoclonal) antibody of the present invention can be prepared by any technique. Techniques for preparing such antibody are well-known in the art (see, for example, Sambrook, J. et al., Molecular Cloning, Cold Spring Harbor Laboratory Press, 1989). The term "monoclonal antibody" used herein is not limited to an antibody prepared by a hybridoma technique. The term "monoclonal antibody" refers to an antibody originating from a single clone (e.g., a clone of a eucaryote, procaryote, or phage), and such antibody can be prepared by any method. The monoclonal antibody of the present invention can be prepared by any of a variety of techniques known in the art. Examples thereof include a hybridoma method, a recombination method, a phage-display method, and a combination of any thereof. All thereof is within the scope of the present invention.

(a) Preparation of Polyclonal Antibody

In order to prepare a polyclonal antibody, cadherin, expression product of the cadherin extracellular domain, or a partial peptide thereof (preferably EC1) is, as the antigen, administered to a mammalian animal, such as a rat, mouse, or rabbit. The amount of the antigen to be administered per animal is 0.1 to 100 mg when no adjuvant is used, and it is 1 to 100 μg when an adjuvant is used. Examples of adjuvant include Freund's complete adjuvant (FCA), Freund's incomplete adjuvant (FIA), and aluminum hydroxide adjuvant. Immunization is carried out primarily via intravenous, hypodermic, or intraperitoneal injection. The interval between two immunization instances is not particularly limited, and immunization is carried out at the interval of several days to several weeks, and preferably at the interval of 2 to 5 weeks 1 to 10 times, and preferably 2 to 5 times. The antibody titer is assayed via enzyme immunoassay (ELISA), radioimmunoassay (RIA) or other techniques 6 to 60 days after the final immunization instance, and the blood sample is collected on the day the maximal antibody titer is assayed in order to obtain antiserum. If necessary, an antibody can be purified from the antiserum by a known technique adequately selected from among, for example, salting out with ammonium sulfate, ion-exchange chromatography, gel filtration, and affinity chromatography. Alternatively, any of these techniques may be performed in adequate combination.

(b) Preparation of Monoclonal Antibody

In order to prepare a monoclonal antibody, cadherin, an expression product of the cadherin extracellular domain, or a partial peptide thereof (preferably EC1) is, as the antigen, administered to a mammalian animal, such as a rat, mouse, or rabbit. The amount of the antigen to be administered per animal is 0.1 to 100 mg when no adjuvant is used, and it is 1 to 100 μg when an adjuvant is used. Examples of adjuvant include Freund's complete adjuvant (FCA), Freund's incomplete adjuvant (FIA), and aluminum hydroxide adjuvant. Immunization is carried out primarily via intravenous, hypodermic, or intraperitoneal injection. The interval between two immunization instances is not particularly limited, and immunization is carried out at the interval of several days to several weeks, and preferably at the interval of 2 to 5 weeks 1 to 10 times, and preferably 2 to 5 times. The antibody producing cells are collected 1 to 60 days, and preferably 1 to 14 days after the final immunization instance. Examples of the antibody producing cells include spleen cells, lymph node cells, and peripheral blood cells, with spleen cells and local lymph node cells being preferable.

In order to obtain fusion hybridoma cells, antibody producing cells and myeloma cells are subjected to cell fusion. As myeloma cells to be fused to the antibody producing cells, generally available established cell lines of animals such as mice can be used. Cell lines preferably have properties as follows. That is, the cell lines that have drug selectivity that cannot survive in HAT selection medium (containing hypoxanthine, aminopterin, and thymidine) in a state of unfusion and can survive only in a state where the cell is fused to the antibody producing cells are preferable. Examples of myeloma cells include mouse myeloma cells, such as P3×63-Ag.8.U1 (P3U1) and NS-1.

Subsequently, the myeloma cells and the antibody producing cells are subjected to cell fusion. Cell fusion is carried out in a medium for animal cell culture, such as serum-free DMEM or RPMI-1640 medium, by mixing the antibody producing cells ($1\times10^6$ to $1\times10^7$ cells/ml) and the myeloma cells ($2\times10^5$ to $2\times10^6$ cells/ml) (the ratio of the antibody producing cells to the myeloma cells is preferably 5:1) in the presence of a cell fusion promoter. An example of a cell fusion promoter that can be used is polyethylene glycol having the average molecular weight of 1,000 to 6,000 Da. Alternatively, a commercially available cell fusion apparatus utilizing electrical stimulation (e.g., electroporation) may be used to allow the antibody producing cells to fuse to the myeloma cells.

Hybridomas of interest are selected from the cells that have been subjected to cell fusion. To this end, a cell suspension is adequately diluted with RPMI-1640 medium containing fetal bovine serum, the resultant is applied to a microtiter plate at the cell density of about $3\times10^5$ cells/well, a selection medium is added to each well, and culture is then conducted while adequately exchanging the selection medium. As a result, the cells grown about 14 days after the initiation of culture in the selection medium can be obtained as hybridomas.

Subsequently, the culture supernatant of the grown hybridomas is screened so as to detect the target antibody. Hybridoma screening may be carried out in accordance with a conventional technique, without particular limitation. For example, part of the culture supernatant contained in the wells containing the cells grown as hybridomas is sampled, and enzyme immunoassays, radioimmunoassays, or the like may be carried out to screen for hybridomas that produce antibodies which bind to the cadherin domain 1 (EC1). Fusion cells are subjected to cloning via limiting dilution or other means, and hybridomas cells which produce monoclonal antibodies can be established at the end.

Monoclonal antibodies can be collected from the established hybridomas by, for example, a conventional cell culture technique or collection of ascites fluid. According to a cell culture technique, hybridomas are cultured in a medium for animal cell culture such as RPMI-1640 medium containing 10% fetal bovine serum, MEM medium, or serum-free medium under general culture conditions (e.g., at 37° C. in the presence of 5% $CO_2$) for 7 to 14 days, and antibodies are obtained from the culture supernatant.

When monoclonal antibodies are to be collected by means of collection of ascites fluid, about $1\times10^7$ hybridoma cells are administered intraperitoneally to animals of the species same as the mammalian animal from which myeloma cells are obtained, in order to allow large quantities of hybridoma cells to grow. The ascites fluid is sampled 1 to 2 weeks thereafter. If the method for collecting antibodies described above requires antibody purification, it can be carried out by a known technique adequately selected from among, for example, salting out with ammonium sulfate, ion-exchange chromatography, gel filtration, and affinity chromatography. Alternatively, any of these techniques may be performed in adequate combination.

The antibody of the present invention is not particularly limited. For example, mouse antibody, human antibody, rat antibody, rabbit antibody, sheep antibody, camel antibody, bird antibody, or an artificially modified gene recombinant antibody intended to lower a heteroantigenicity against human, such as chimeric antibody or humanized antibody, may be used. A gene recombinant antibody can be produced by a known technique. A chimeric antibody is composed of the heavy chain and the light chain variable regions of a non-human mammalian animal, such as a mouse antibody, and the heavy chain and the light chain constant regions of a human antibody. Such antibody can be obtained by linking DNA encoding a variable region of the mouse antibody to DNA encoding a constant region of the human antibody, inserting the resultant into an expression vector, and introducing the expression vector into a host cell. A humanized antibody is prepared by transplanting a complementarity determining region (CDR) of a non-human mammalian animal, such as a mouse antibody, into the complementarity determining region of a human antibody, and a general gene recombination technique therefor has been known. Specifically, a DNA sequence that is designed to link a CDR of a mouse antibody to a framework region (FR) of a human antibody is synthesized via PCR from several oligonucleotides prepared so as to have overlapping regions at the terminuses. The obtained DNA is linked to DNA encoding a constant region of a human antibody, the resultant is inserted into an expression vector, and the expression vector is then introduced into a host cell. Thus, a humanized antibody is prepared (e.g., EP 239400 and WO 96/02576).

CH of a humanized chimeric antibody may be human immunoglobulin of any type (hereafter, referred to as "hIg"), CH of the class hIgG is preferable, and any of the subclasses hIgG1, hIgG2, hIgG3, and hIgG4 of the class hIgG can be used. CL of a humanized chimeric antibody may be any hIg, and that of the class κ or λ can be used.

The CDR-transplanted humanized antibody is prepared by transplanting the amino acid sequences of the VH and VL CDRs of a non-human animal antibody into adequate positions of the VH and the VL of a human antibody.

The CDR-transplanted humanized antibody can be prepared by constructing cDNA encoding a V region resulting from transplantation of the amino acid sequences of the VH and VL CDRs of a non-human animal antibody reacting specifically with cadherin into the VH and VL FRs of any human antibody, inserting the resultants into an animal cell expression vector having DNA encoding CH and CL of the human antibody so as to construct a vector expressing the CDR-transplanted humanized antibody, and introducing and expressing the resultant in an animal cell.

Many antibody-producing host cells that are used for protein expression originate from mammalian animals. The specific host cell that is the most optimal for the gene expression product of interest can be preferentially determined. Examples of general host cells include, but are not limited to, the cell line originating from the CHO cell (Chinese hamster ovary cell), the CV1 (monkey kidney cell), COS (a derivative of CV1 harboring the SV40 T antigen), SP2/0 (mouse myeloma cell), P3x63-Ag3.653 (mouse myeloma cell), 293 (human kidney cell), and 293T (a derivative of 293 harboring the SV40 T antigen). Host cells can be obtained from commercial institutions, the American Tissue Culture Collection (ATCC), or an organization that has published a relevant document.

A preferable host cell is either the DGFR-deficient cell line originating from the CHO cell, or SP2/0 (see Urland, G et al., Effect of gamma rays at the dihydrofolate reductase locus: deletions and inversions, Somat. Cell. Mol. Genet. Vol. 12, 1986, pp. 5555-566; and Schulman, M. et al., A better cell line for making hybridomas secreting specific antibodies, Nature, Vol. 276, 1978, pp. 269-270). The most preferable host cell is the DGFR-deficient CHO cell.

A plasmid can be transfected into a host cell by any technique. Specific examples include, but are not limited to, transfection (including the calcium phosphate method, the DEAE method, lipofection, and electroporation), a method comprising introduction of DNA with the use of an envelop such as the Sendai virus, microinjection, and infection using a virus vector such as a retrovirus or adenovirus vector (see Current Protocols in Molecular Biology, Chapter 9: Introduction of DNA into Mammalian Cells, John Wiley and Sons, Inc.). Introduction of a plasmid into a host cell via electroporation is the most preferable.

An example of another technique for preparing a humanized or chimeric antibody is a method wherein the interactions between CDRs and framework residues are modeled in order to identify important framework residues for antigen linking, and sequences are compared to identify unusual framework residues located at specific positions (e.g., Queen et al., U.S. Pat. Nos. 5,530,101, 5,585,089, 5,693,761, 5,693,762, and 6,180,370; all patents are incorporated herein by reference in their entirety). Antibodies can be humanized by a variety of techniques known in the art. Examples of such techniques include CDR grafting (European Patent No. 239, 400; PCT International Publication WO 91/09967; and U.S. Pat. Nos. 5,225,539, 5,530,101, and 5,585,089), veneering or resurfacing (European Patent Nos. 592,106 and 519,596; Padlan, Mol. Immunol., vol. 28, pp. 489 to 498, 1991; Studnicka et al., Prot. Eng., vol. 7, pp. 805 to 814, 1994; Roguska et al., Proc. Natl. Acad. Sci., vol. 91, pp. 969 to 973, 1994), and chain shuffling (U.S. Pat. No. 5,565,332). A method for preparing a chimeric antibody is described in Molecular Biotechnology 26, 39, 2004 and Journal of Immunological Methods 125, 191, 1989. These documents are incorporated herein by reference in their entirety.

It is preferable that the amino acid sequence of the chimeric or humanized antibody be completely identical to the amino acid sequence of the VH or VL region originating from cDNA expressed by the deposited hybridoma. An antibody having a sequence exhibiting 90% or higher identity as a result of genetic engineering is also preferable. In the course of humanization or chimerization, adjustment of residue substitution has heretofore been performed aimed at improvement of antigen linking since such antibody with a partially modified sequence is considered to be fundamentally derived from the original hybridoma.

Techniques for preparing a chimeric or humanized antibody via genetic engineering have been known. Specifically, the VH and VL sequences of the original monoclonal antibody are genetically engineered and then chimeralized or humanized in accordance with a conventional technique.

A method for obtaining a human antibody is also known. For example, human lymphocytes are subjected to sensitization with antigens of interest or with cells expressing antigens of interest in vitro, the sensitized lymphocytes are fused to human myeloma cells such as U266 cells, and a human antibody of interest having activity of binding to an antigen can then be obtained (see JP Patent Publication (Kokoku) No. H01-59878 B (1989)). Alternatively, a transgenic animal having the entire repertoire of human antibody genes may be immunized with an antigen of interest to obtain a human antibody of interest (see WO 93/12227, WO 92/03918, WO 94/02602, WO 94/25585, WO 96/34096, and WO 96/33735). In addition, a technique for obtaining a human antibody via panning using human antibody libraries has been known. For example, a human antibody variable region is expressed on the phage surface by the phage display method as a single chain antibody (scFv), and a phage which binds to antigen can be selected. The gene of the selected phage may be analyzed so as to determine the DNA sequence encoding a variable region of the human antibody which binds to the antigen. Upon elucidation of the DNA sequence of scFv which binds to antigen, an adequate expression vector can be prepared based on such sequence and a human antibody can then be obtained. Such techniques have been well-known in the art. See WO 92/01047, WO 92/20791, WO 93/06213, WO 93/11236, WO 93/19172, WO 95/01438, and WO 95/15388.

Such antibody may be monovalent, divalent or polyvalent, provided that it recognizes a cadherin domain 1 (EC1) of cadherin and maintains a high internalization capacity. An antibody may be a low-molecular antibody such as antibody fragment, or a modified antibody. Examples of antibody fragments include Fab, Fab', $F(ab')_2$, scFv, dsFv, and a peptide comprising CDR. Alternatively, an Fc region is fused to an antibody fragment or a low-molecular antibody, such as Fab, Fab', $F(ab')_2$, Fv, scFv (single chain Fv), or diabody, to provide them with ADCC activity. In order to attain such antibody, a gene encoding such antibody may be constructed, the resultant may be introduced into an expression vector, and the resultant may be incorporated into the expression vector and may be expressed in an adequate host cell.

Among fragments obtained by processing IgG with a protease, papain (cut at amino acid 224 of the H chain), Fab is an antibody fragment having a molecular weight of about 50,000 and having antigen-binding activity, which is composed of about a half of the N-terminal side of the H chain bound to the entire L chain through a disulfide bond.

Fab of the present invention can be obtained by processing an antibody which specifically reacts with cadherin, with a protease, papain. Alternatively, DNA encoding Fab of the antibody may be inserted into a procaryote or eucaryote expression vector, and the vector may be introduced and expressed in a procaryote or eucaryote. Thus, Fab can be prepared.

Among the fragments obtained by processing IgG with a protease, pepsin (cut at amino acid 234 of the H chain), $F(ab')_2$ is an antibody fragment having a molecular weight of about 100,000 and having antigen-binding activity, which is somewhat larger than the product obtained by binding two Fab via a disulfide bond of the hinge region.

$F(ab')_2$ of the present invention can be obtained by processing an antibody which specifically reacts with cadherin, with a protease, pepsin. Alternatively, it can be prepared by binding two Fab' described below via thioether or disulfide.

Fab' is an antibody fragment having a molecular weight of about 50,000 and having antigen-binding activity resulting from the cleavage of a disulfide bond of $F(ab')_2$ of the hinge region mentioned above.

Fab' of the present invention can be obtained by processing $F(ab')_2$ which specifically reacts with cadherin, with a reducing agent, dithiothreitol. Alternatively, DNA encoding the Fab' fragment of the antibody may be inserted into a procaryote or eucaryote expression vector, and the vector may be introduced into a procaryote or eucaryote to express Fab' therein. Thus, Fab' can be prepared.

"scFv" indicates a VH-P-VL or VL-P-VH polypeptide composed of a single VH linked to a single VL via an adequate peptide linker (herein referred to as "P"). VH and VL included in the scFv of the present invention can be derived from the antibody of the present invention which specifically reacts with cadherin, such as a humanized antibody or human antibody.

The scFv of the present invention can be prepared by obtaining cDNA encoding VH and VL of an antibody which specifically reacts with cadherin, constructing DNA encoding scFv, inserting the DNA into a procaryote or eucaryote expression vector, and introducing the vector into a procaryote or eucaryote to express scFv therein.

"dsFv" is obtained by binding the polypeptides where a single amino acid residue in VH and VL is substituted with a cysteine residue to each other via a disulfide bond between the cysteine residues. Amino acid residues to be substituted with cysteine residues can be selected in accordance with the method of Reiter et al. (Protein Engineering, 7, 697, 1994) based on the prediction of the antibody conformation. VH and VL included in the dsFv of the present invention can be derived from the antibody of the present invention which specifically react with cadherin such as a humanized or human antibody.

The dsFv fragment of the present invention can be prepared by obtaining cDNA encoding VH and VL of an antibody which specifically reacts with cadherin, constructing DNA encoding dsFv, inserting the DNA into a procaryote or eucaryote expression vector, and introducing the vector into a procaryote or eucaryote to express dsFv therein.

A peptide comprising CDR is composed of at least one of the H or L chain CDR. A plurality of CDRs can be linked directly to each other or via an adequate peptide linker.

The peptide comprising CDR of the present invention can be prepared by obtaining cDNA encoding VH and VL of the antibody which specifically reacts with cadherin, constructing DNA encoding CDR, inserting the DNA into a procaryote or eucaryote expression vector, and introducing the vector into a procaryote or eucaryote to express such peptide therein.

The peptide comprising CDR can also be produced via chemical synthesis, such as the Fmoc (fluorenylmethyloxycarbonyl) method or the tBoc (t-butyloxycarbonyl) method.

As a modified antibody, an antibody conjugated to a various molecule, such as polyethylene glycol (PEG), can also be used. A drug-conjugated antibody is particularly useful. Such modified antibody can be obtained by subjecting an antibody to chemical modification. A method of antibody modification is known in the art.

The antibody of the present invention exerts a high internalization capacity. Thus, a toxin may be conjugated thereto, and the resultant may be used in the form of a cytotoxic agent. The cytotoxic agent of the present invention may be brought into contact with, for example, cadherin-expressing cancer cells, so that the agent can damage the cancer cells.

According to a preferable embodiment of the present invention, the antibody is a so-called ADC comprising an antibody and a cytotoxic substance such as a drug conjugated thereto.

Examples of drugs that can be used in the present invention include, but are not limited to, duocarmycin, a duocarmycin analogue, a duocarmycin derivative, CC-1065, a duocarmycin analogue mainly composed of CBI, a duocarmycin analogue mainly composed of MCBI, a duocarmycin analogue mainly composed of CCBI, doxorubicin, a doxorubicin conjugate, morpholino-doxorubicin, cyanomorpholino-doxorubicin, dolastatin, dolestatin-10, combretastatin, calicheamicin, maytansine, a maytansine analogue, DM1, DM2, DM3, DM4, DMI, auristatin E, auristatin EB (AEB), auristatin EFP (AEFP), monomethyl auristatin E (MMAE), monomethyl auristatin F (MMAF), 5-benzoylvaleric acid-AE ester (AEVB), tubulysin, disorazole, epothilone, paclitaxel, docetaxel, SN-38, topotecan, rhizoxin, echinomycin, colchicine, vinblastine, vindesine, estramustine, cemadotin, eleutherobin, methotrexate, methopterin, dichloromethotrexate, 5-fluorouracil, 6-mercaptopurine, cytosine arabinoside, melphalan, leurosine, leurosideine, actinomycin, daunorubicin, a daunorubicin conjugate, mitomycin C, mitomycin A, carminomycin, aminopterin, tallysomycin, podophyllotoxin, a podophyllotoxin derivative, etoposide, etoposide phosphate, vincristine, taxol, taxotere retinoic acid, butyric acid, $N^8$-acetyl spermidine, and camptothecin.

The ADC used in the present invention can be prepared by binding the aforementioned drug to an antibody in accordance with a conventional technique. An antibody and a drug may be directly bound to each other via their own linker groups or indirectly via a linker or other substance.

A drug may be directly bound to an antibody via a disulfide bond between SH or via maleimide groups. For example, the intramolecular disulfide bond in the Fc region of an antibody and the disulfide bond of a drug may be reduced, and the drug may be bound to the antibody via a disulfide bond. Alternatively, they may be bound to each other via maleimides. Further, cysteine may be introduced into an antibody via genetic engineering.

An antibody can be bound to a drug indirectly via another substance (linker). A linker preferably comprises one or more functional groups that react with either or both of the antibody and the drug. Examples of functional groups include amino, carboxyl, mercapto, maleimide, and pyridinyl groups.

Examples of linkers include, but are not limited to, sulfo-succinimidyl-4-(N-maleimidomethyl)cyclohexane-1-carboxylate (Sulfo-SMCC), N-succinimidyl-4-(maleimidomethyl)cyclohexanecarboxylate (SMCC), N-succinimidyl-4-(N-maleimidomethyl)-cyclohexane-1-carboxy-(6-amidocaproate) (LC-SMCC), κ-maleimidoundecanoic acid N-succinimidyl ester (KMUA), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl-6-β-maleimidopropionamido)hexanoate (SMPH), N-succinimidyl-4-(p-maleimidophenyl)-butyrate (SMPB), N-(p-maleimidophenyl)isocyanate (PMPI), 6-maleimidocaproyl (MC), maleimidopropanoyl (MP), p-aminobenzyloxycarbonyl (PAB), N-succinimidyl-4-(2-pyridylthio)pentanoate (SPP), and N-succinimidyl(4-iodoacetyl) aminobenzoate (SIAB). A peptide linker such as valine-citrulline (Val-Cit) or alanine-phenylalanine (ala-phe) may also be used, and any of the aforementioned linkers may be used in adequate combination.

A drug can be bound to an antibody in accordance with the method described in, for example, Cancer Research, 68 (22) 9280, 2008, Nature Biotechnology, 26 (8) 925, 2008, Bio Conjugate Chemistry, 19, 1673, 2008, Cancer Research, 68 (15), 6300, 2008, or JP Patent Publication (Kohyo) No. 2008-516896 A.

Another embodiment of the antibody-drug conjugate of the present invention is a so-called "immunotoxin" composed of an antibody and a toxin linked thereto chemically or via genetic engineering.

Examples of toxins that can be used in the present invention include diphtheria toxin A-chain, *Pseudomonas* endotoxin, ricin chain, deglycosylated ricin A chain, gelonin, and saporin.

Another embodiment of the antibody of the present invention is a so-called "RI-labeled antibody" composed of the antibody of the present invention and a radioactive substance labeled thereto.

When a radioactive substance is used in the form of a cancer therapeutic agent, a cytotoxic radioactive metal is preferable. When it is used in the form of a cancer diagnostic agent, a non-cytotoxic radioactive metal is preferable. Iodine 123 (123I) or iodine 131 (131I) may also be used.

Examples of cytotoxic radioactive metals include yttrium 90 (90Y), rhenium 186 (186Re), rhenium 188 (188Re), copper 67 (67Cu), iron 59 (59Fe), strontium 89 (89Sr), gold 198

(198Au), mercury 203 (203Hg), lead 212 (212Pb), dysprosium 165 (165Dy), ruthenium 103 (103Ru), bismuth 212 (212Bi), bismuth 213 (213Bi), holmium 166 (166Ho), samarium 153 (153Sm), and lutetium 177 (177Lu).

Among these radioactive metals, 90Y, 153Sm, and 177Lu are particularly preferable from the viewpoint of, for example, half-life, radioactive energy, ease of labeling, the labeling efficiency, or stability of a complex.

Examples of preferable non-cytotoxic radioactive metals as the diagnostic agents include, but are not limited to, technetium 99m (99mTc), indium 111 (111In), indium 113m (113mIn), gallium 67 (67Ga), gallium 68 (68Ga), thallium 201 (201Tl), chromium 51 (51Cr), cobalt 57 (57Co), cobalt 58 (58Co), cobalt 60 (60Co), strontium 85 (85Sr), mercury 197 (197Hg), and copper 64 (64Cu).

In order to bind such radioactive metal element to the antibody of the present invention, it is preferable that a metal chelating reagent be allowed to react with the antibody and the radioactive metal element be allowed to react therewith to form a complex. In the modified antibody thus obtained, a radioactive metal element is bound to the antibody of the present invention via a metal chelating reagent.

Examples of metal chelating reagents used for formation of such a complex include: (1) quinoline derivatives, such as 8-hydroxyquinoline, 8-acetoxyquinoline, 8-hydroxyquinaldine, oxyquinoline sulfate, O-acetyloxine, O-benzoyloxine, O-p-nitrobenzoyloxine, and quinolone compounds having a quinoline skeleton (e.g., norfloxacin, ofloxacin, enoxacin, ciprofloxacin, lomefloxacin, tosfloxacin, fleroxacin, and sparfloxacin); (2) compounds, such as chloranilic acid, aluminon, thiourea, pyrogallol, cupferron, Bismuthiol (II), galloyl gallic acid, thiolide, 2-mercaptobenzothiazole, and tetraphenylarsonium chloride; (3) ethylenediaminetetraacetic acid (EDTA), diethylenetriaminepentaacetic acid (DTPA), and compounds having a similar skeleton (dihydroxyethylglycine, diaminopropanol tetraacetic acid, ethylenediamine diacetic acid, ethylenediaminedipropionic acid hydrochloride, hydroxyethylethylenediaminetriacetic acid, ethylenediaminetetrakis(methylenesulfonic acid), glycol ether diaminetetraacetic acid, hexamethylenediaminetetraacetic acid, hydroxyethyliminodiacetic acid, iminodiacetic acid, diaminopropanetetraacetic acid, nitrilotriacetic acid, nitrilotripropionic acid, nitrilotris(methylenesulfonic acid) trisodium salt, triethylenetetraminehexaacetic acid, methyl DTPA, cyclohexyl DTPA, aminobenzyl EDTA, isothiocyanobenzyl EDTA, isothiocyanobenzyl DTPA, methylisothiocyanobenzyl DTPA, cyclohexylisothiocyanobenzyl DTPA, maleimidopropylamidobenzyl EDTA, maleimidopentylamidobenzyl EDTA, maleimidodecylamidobenzyl EDTA, maleimidopentylamidobenzyl DTPA, maleimidodecylamidobenzyl EDTA, and maleimidodecylamidobenzyl DTPA); and (4) 1,4,7,10-tetraazacyclododecane-1,4,7,10-tetraacetic acid (DOTA), 1,4,7-triazacyclononane-1,4,7-triacetic acid (NOTA), 1,4,8,11-tetraazacyclotetradecane-1,4,8,11-tetraacetic acid (TETA), 1,4,7,10-tetraazacyclododecane (Cyclen), 1,4,8,11-tetraazacyclotetradecan (Cyclam), isothiocyanobenzyl DOTA, and isothiocyanobenzyl NOTA.

Among these metal-chelating reagents, isothiocyanobenzyl DOTA, methylisothiocyanobenzyl DTPA, and cyclohexylisothiocyanobenzyl DTPA are preferable from the viewpoint of, for example, ease of introduction of a metal chelate into an antibody, the labeling efficiency, or stability of a complex.

A person skilled in the art would be able to bind a radioactive metal element to the antibody of the present invention in accordance with a conventional technique. For example, a metal chelating reagent is allowed to react with the antibody of the present invention to thereby prepare a label precursor in advance, and the precursor is then allowed to react with a radioactive metal element.

The cytotoxic agent of the present invention can adequately contain a pharmaceutically acceptable carrier, an excipient, a diluent, or the like, according to need, in addition to the antibody of the present invention (to which a cytotoxic substance, including a drug, toxin, or radioactive substance, may be bound according to need). The cytotoxic agent of the present invention can be prepared in the form of an injection preparation, for example. The dose of the cytotoxic agent of the present invention varies depending on the symptoms, severity, age, and body weight of a patient, the route of administration, or other factors. The weight of the antibody as an active ingredient is generally about 10 ng to about 100 mg/kg (body weight).

The pharmaceutical composition of the present invention is particularly useful as a therapeutic agent for diseases with high expression of cadherin (preferably CDH3). The diseases with high expression of cadherin (preferably CDH3) are not particularly limited, with cancer being preferable. Examples of such diseases include colon cancer, breast cancer, ovarian cancer, endometrial cancer, uterine cervix cancer, lung cancer, transitional cell cancer, pancreatic cancer, hepatic cancer, renal cancer, biliary tract cancer, thyroid gland cancer, head and neck cancer, esophageal cancer, cutaneous squamous cell cancer, melanoma, gastric cancer, prostate cancer, osteosarcoma, and soft tissue sarcoma.

Hereafter, the present invention is described in greater detail with reference to the following examples, although the present invention is not limited thereto.

EXAMPLES

Example 1

Expression of Human CDH3 mRNA in Normal Tissue and Cancer Tissue

Figure 3C:
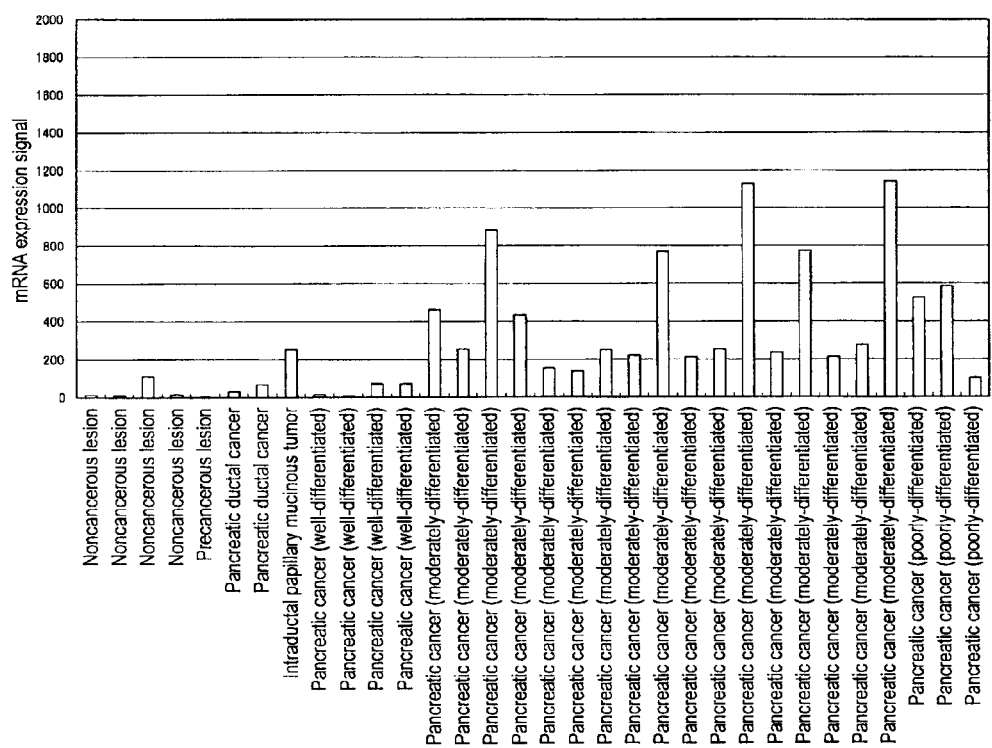
FIG. 3 shows the results of human CDH3 mRNA expressed in various types of tumor tissues (A: normal tissues; B: various types of cancer tissues; and C: the degree of differentiation of pancreatic cancer cells).

Total RNA samples were prepared in accordance with a conventional technique with the use of Isogen (Nippon Gene) from the samples collected from normal human tissues and various types of cancer tissues via laser capture microdissection. The RNA samples (10 ng each) were subjected to gene expression analysis using the GeneChipU-133B (Affymetrix, Inc.) in accordance with the Expression Analysis Technical Manual (Affymetrix, Inc.). The average expression level of all the genes was designated to be 100, and the genes exhibiting the enhanced expression levels in cancer cells were screened for. As a result, human CDH3 expression was found to be limited in normal human tissues, but the expression levels thereof were found to be enhanced in lung cancer, colon cancer, and pancreatic cancer cells (FIGS. 3A and 3B). Also, CDH3 mRNA expression in pancreatic cancer tissue with different degrees of differentiation was examined. As a result, the expression levels thereof were found to be high in some tissues, regardless of degrees of differentiation (FIG. 3C).

Example 2

Expression of Human CDH3 Protein in Cancer Tissue Analyzed via Immunohistochemical Staining In order to inspect CDH3 protein expression in clinical cancer specimens, immunostaining was carried out with the use of arrays containing cancer tissue specimens.

The arrays containing tissue specimens of pancreatic cancer (glandular cancer), lung cancer (glandular cancer), lung cancer (squamous cell cancer), and colon cancer (glandular cancer) obtained from Shanghai Outdo Biotech Co., Ltd.) were used.

The tissue array slides were subjected to deparaffinization and then activation with 10 mM Tris and 1 mM EDTA (pH 9.0) at 95° C. for 40 minutes. After endogenous peroxidase was inactivated with the use of a blocking reagent included in the Envision+kit (Dako), the samples were allowed to react with 5 µg/ml anti-CDH3 antibody 610227 (BD Biosciences) or with 5 µg/ml anti-HBs antibody Hyb-3423 (a negative control) at 4° C. overnight. After the antibody solution was washed away, the samples were allowed to react with a polymer secondary antibody reagent included in the Envision+ kit at room temperature for 30 minutes. The samples were then subjected to color development using a coloring reagent included in the Envision+ kit, and nuclear staining was performed with the use of a hematoxylin/eosin solution.

Figure 4:
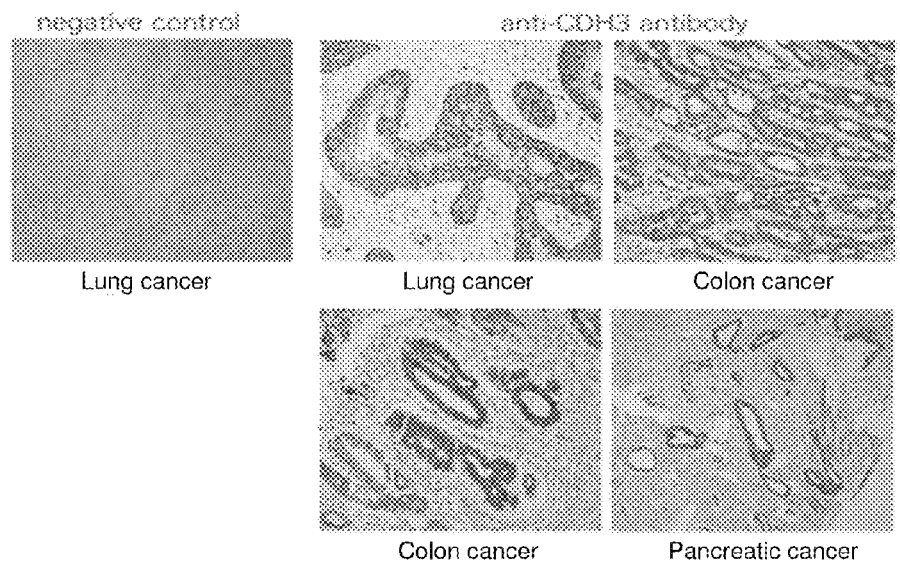
FIG. 4 shows the results of immunostaining of human CDH3 in various types of tumor tissues.

FIG. 4 shows the results. While cancer cells were stained with the anti-human CDH3 antibody, normal cells were not stained therewith.

Example 3

Establishment of Human CDH3-Expressing CHO Cell Line

In order to obtain a cell line for anti-CDH3 antibody screening, a CHO cell line expressing full-length CDH3 was established.
(1) Production of CDH3 Gene Expression Vector In order to insert full-length human CDH3 DNA as shown in SEQ ID NO: 1 into a mammal expression vector pEF4/myc-HisB (Invitrogen), the full-length human CDH3 DNA was treated with two restriction enzymes KpnI (Takara Bio Inc.) and XbaI (Takara Bio Inc.) at 37° C. for 1 hour. Thereafter, the thus-obtained fragment was inserted into pEF4/myc-HisB, which had been treated with the same restriction enzymes KpnI and XbaI, with use of T4 DNA ligase (Promega) in accordance with a conventional technique. Thus, an expression vector (pEF4-CDH3-myc-His) was obtained.
(2) Acquisition of Stable CDH3-Expressing Cell Line In accordance with the protocol of a FuGENE® 6 transfection reagent (Roche Diagnostics K.K.), $8\times10^5$ CHO cells were inoculated into a 10-cm diameter dish on the day before transfection, and the cells were cultured overnight. Thereafter, 8 µg of an expression vector (pEF4-CDH3-myc-His) and 16 µl of an FuGENE 6 regent were mixed with 400 µl of serum-free RPMI 1640 medium (Sigma-Aldrich), and the mixture was allowed to stand at room temperature for 15 minutes. The resultant was added to the cell culture solution for transfection. Two days after transfection, cloning was performed through limiting dilution with the use of a selection reagent (Zeocin®).

Figure 5:
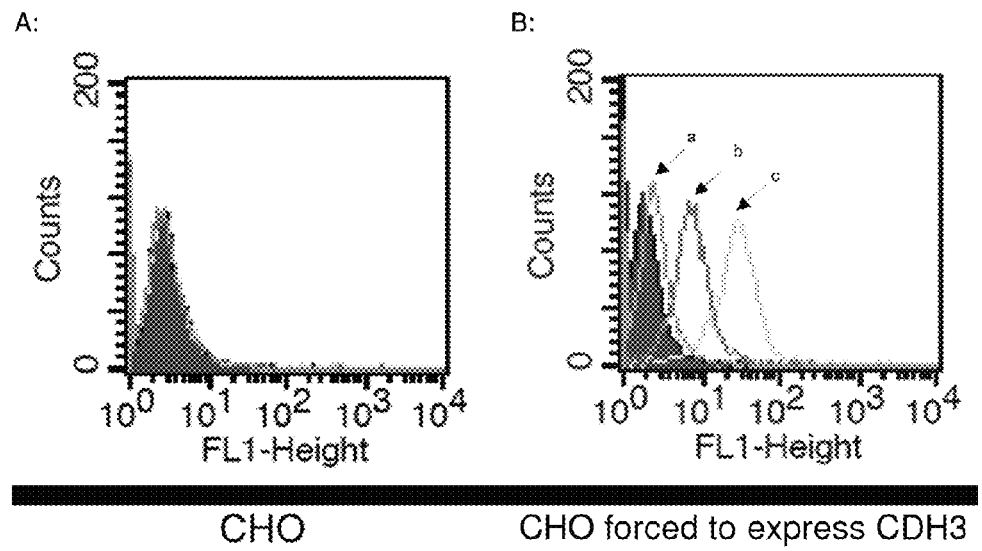
FIG. 5 shows the results of flow cytometric analysis based on the reaction of cell lines forced to express human CDH3 and a commercially available anti-human CDH3 antibody (A: CHO cells; B: CHO cells forced to express human CDH3; a: 0.01 mg/ml anti-human CDH3 antibody; b: 0.1 mg/ml anti-human CDH3 antibody; and c: 1 mg/ml anti-human CDH3 antibody).

Clones of full-length CDH3-expressing CHO cells were selected through Western blotting with the use of an anti-c-Myc monoclonal antibody (Santa Cruz Biotechnology, Inc.). As a result, a CHO cell line (EXZ1501) forced to express CDH3, which exhibits a high expression level and a high growth capacity, was obtained. The obtained cell line, its parental strain (i.e., CHO), and a commercially available anti-CDH3 antibody (R&D Systems, Inc.) were subjected to the reaction and analyzed by flow cytometry. The results are shown in FIG. 5.

Example 4

Production of Human CDH3 Extracellular Domain Antigen

The human CDH3 extracellular domain protein (sCDH3) which lacks the C-terminal transmembrane region and a region subsequent thereto was produced to serve as an immunogen for production of an anti-human CDH3 antibody.
(1) Production of sCDH3 Antigen Expression Vector PCR was performed with the use of a human CDH3 full-length cDNA as a template and a forward primer (SEQ ID NO: 7: CGCGGTACCATGGGGCTCCCTCGT) and a reverse primer (SEQ ID NO: 8: CCGTCTAGATAACCTC-CCTTCCAGGGTCC), which had been designed so as to amplify a fragment corresponding to the human CDH3 extracellular domain (1-654 in SEQ ID NO: 2, hereinafter referred to as sCDH3 cDNA). The reaction was carried out with the use of KOD-Plus (Toyobo Co., Ltd.) by repeating a cycle of 94° C. for 15 seconds, 55° C. for 30 seconds, and 68° C. for 90 seconds 30 times.

Thereafter, a gel fragment containing a band of a target size (about 2.0 kbp) was cleaved via agarose gel electrophoresis, and the target sCDH3 cDNA was obtained using a QIA® quick gel extraction kit (QIAGEN K.K.).

In order to insert sCDH3 cDNA into a pEF4/myc-HisB expression vector, sCDH3 cDNA was treated with two restriction enzymes KpnI and XbaI. The thus-obtained fragment was then inserted into pEF4/myc-HisB, which had been treated with the same restriction enzymes KpnI and XbaI, with the use of T4 DNA ligase in accordance with a conventional technique, and a pEF4-sCDH3-myc-His expression vector was obtained.
(2) Expression of Soluble CDH3 Protein In accordance with the protocol of a FuGENE 6 transfection reagent, $8\times10^5$ CHO cells were inoculated into a 10-cm dish on the day before transfection, and the cells were cultured overnight. Thereafter, 8 µg of a pEF4-sCDH3-myc-His expression vector and 16 µl of a FuGENE 6 regent were mixed with 400 µl of serum-free RPMI 1640 medium, and the mixture was allowed to stand at room temperature for 15 minutes. The resultant mixture was added to the cell culture solution for transfection. Two days after transfection, cloning was carried out through limiting dilution with the use of a selection reagent (Zeocin®).

Soluble CDH3-expressing CHO cells were selected via Western blotting with the use of an anti-c-Myc monoclonal antibody (Santa Cruz Biotechnology, Inc.). Cell lines which exhibit high levels of secretion into the culture supernatant and high proliferation were selected to obtain soluble CDH3-expressing CHO cell lines (EXZ1702). The selected EXZ1702 cell lines were cultured for 72 hours in three roller bottles (each culture area: 1,500 $cm^2$) with serum-free medium CHO-S-SFM-II (333 ml/bottle) (Invitrogen), and the culture supernatants were recovered. The thus-obtained culture supernatants were subjected to affinity chromatography by means of the HisTrap® HP column (GE Healthcare Biosciences Inc.) and gel filtration chromatography by means of Superdex® 200 pg column (GE Healthcare Biosciences Inc.). Thus, soluble CDH3 extracellular domain protein was obtained.

Example 5

Production of Anti-Human CDH3 Monoclonal Antibody (1) Production of Monoclonal Antibody Using Soluble CDH3 Protein as Immunogen A solution of 50 μg of soluble CDH3 proteins dissolved in physiological saline was mixed with an equal amount of Titer-MAX Gold® (TiterMax, Inc.), and the mixture was intraperitoneally and hypodermically injected to MRL/lpr mice (Japan SLC Inc.) for the initial immunization. Subsequent immunization procedures were performed by injecting a similarly prepared mixture of soluble CDH3 protein (25 μg) and Titer-MAX Gold® intraperitoneally and hypodermically to the mice. Three days after the final immunization, spleen cells were prepared from the mice under aseptic conditions, and the cells were fused with mouse myeloma cells SP2/O-Ag14 or P3-X63-Ag8.653 in accordance with a conventional technique by the polyethylene glycol method).

(2) Selection of Anti-Human CDH3 Antibody-Producing Hybridoma

Selection of anti-human CDH3 antibodies was performed via flow cytometric analysis with the use of EXZ1501.

Specifically, EXZ1501 was removed from a culture plate via treatment thereof with 2 mM EDTA-PBS and then suspended in an FACS solution to a cell density of $1 \times 10^6$ cells/ml. The cell suspension was inoculated into a 96-well plate to a density of 50 μl/well, a hybridoma culture supernatant was added thereto, and the reaction was allowed to proceed at 4° C. for 60 minutes. After the plate was washed twice with the FACS solution (200 μl/well), Alexa Fluor 488-labeled anti-mouse IgG.goat F(ab')$_2$ (Invitrogen) was added thereto, and the reaction was allowed to proceed at 4° C. for 30 minutes. Thereafter, the plate was washed twice with the FACS solution, flow cytometric analysis was performed, and hybridomas which are observed to react with EXZ1501 were selected.

Figure 6:
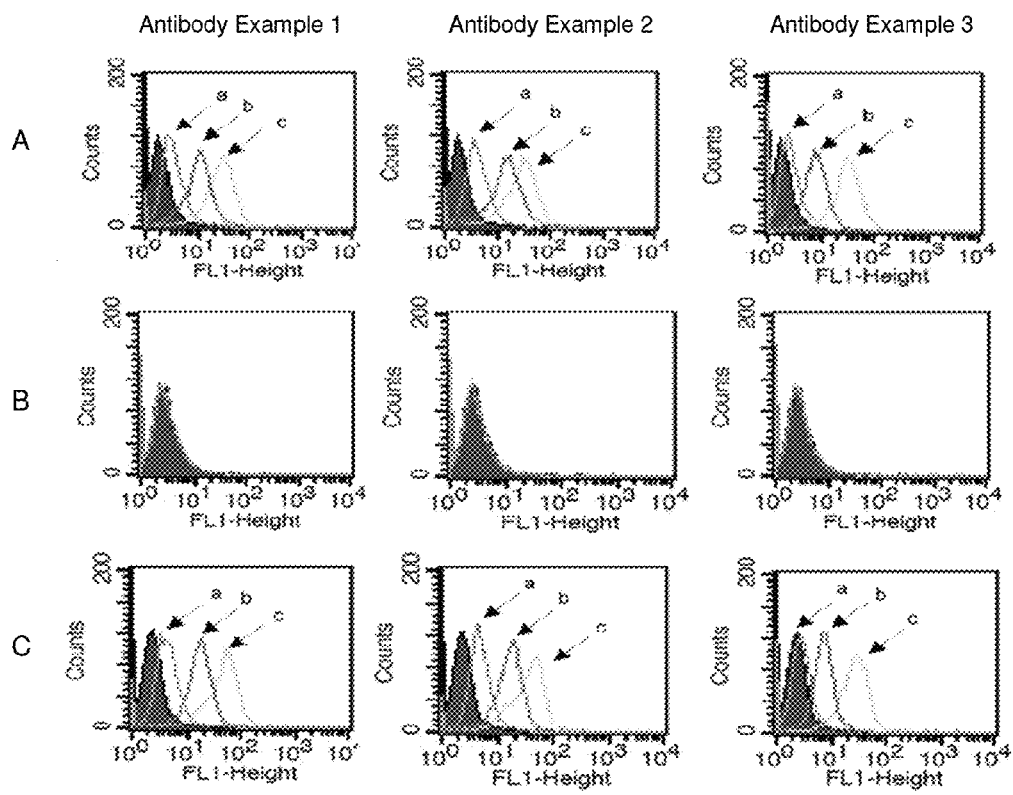
FIG. 6 shows the results of typical flow cytometric analysis based on the reaction of 3examples of antibodies obtained and various cell lines (A: CHO cells forced to express human CDH3; B: CHO cells; C: NCI-H358 lung cancer cell line; a: 0.01 mg/ml anti-human CDH3 antibody; b: 0.1 mg/ml anti-human CDH3 antibody; and c: 1 mg/ml anti-human CDH3 antibody).

FIG. 6 shows the results of typical reactions between the antibodies obtained from such hybridomas and EXZ1501, its parental cell strain (the CHO cell), or the human bronchiolo-alveolar adenocarcinoma cell line (NCI-H358) in which a high CDH3 expression level is observed. All the selected hybridomas were found to react with EXZ1501 and NCI-H358; however, these cells did not react with the CHO cell.

Example 6

Evaluation of Internalization Capacity of Anti-Human CDH3 Mouse Antibody Using Saporin-Labeled Anti-Mouse IgG Antibody (MabZAP)

The internalization capacity was assayed with the use of the anti-mouse IgG antibody labeled with a toxin (saporin) that inhibits protein synthesis. Destruction of cells by saporin always involves cellular internalization. Thus, the extent of the human CDH3 expressing cells destroyed by the anti-human CDH3 antibody may be assayed using MabZAP (Advanced Targeting Systems, Inc.) as the secondary antibody, and the internalization capacity of the anti-human CDH3 antibody can be evaluated.

As human CDH3 expressing cells, the HCC1954 human breast cancer cells (5,000 cells/well) were used, 100 ng of the anti-human CDH3 mouse antibodies and 100 ng of MabZAP were added thereto, and the resultant was heated in an incubator at 37° C. in the presence of 5% $CO_2$ for 3 days. Thereafter, activity of an antibody for cell destruction was evaluated using a viable cell counting reagent (Cell Counting Kit-8, DOJINDO LABORATORIES, Inc.). Cell destruction activity was expressed relative to 100% cell viability attained without the addition of antibody. Table 1, FIG. 7A, and FIG. 7B show the results of assays carried out multiple times using different antibodies.

TABLE 1

| Antibody No. | Subtype | Cell viability (%, Test A) | Cell viability (%, Test B) |
|---|---|---|---|
| PPAT-055-01 | IgG1 | 92 | 85 |
| PPAT-055-02 | IgG2a | 31 | 42 |
| PPAT-055-03 | IgG1 | 34 | 50 |
| PPAT-055-05 | IgG1 |  | 69 |
| PPAT-055-07 | IgG2a |  | 45 |
| PPAT-055-08 | IgG2a | 43 | 40 |
| PPAT-055-09 | IgG1 | 26 | 57 |
| PPAT-055-10 | IgG1 |  | 61 |
| PPAT-055-11 | IgG1 |  | 59 |
| PPAT-055-12 | IgG2a | 47 | 58 |
| PPAT-055-13 | IgG1 | 99 | 95 |
| PPAT-055-14 | IgG1 |  | 87 |
| PPAT-055-15 | IgG1 | 23 |  |
| PPAT-055-16 | IgG1 | 88 | 89 |
| PPAT-055-17 | IgG1 | 93 | 87 |
| PPAT-055-18 | IgG1 |  | 65 |
| PPAT-055-19 | IgG2b | 85 | 79 |
| PPAT-055-20 | IgG2a |  | 78 |
| PPAT-055-21 | IgG2a |  | 57 |
| PPAT-055-24 | IgG2a |  | 44 |
| PPAT-055-25 | IgG1 |  | 54 |
| NegativeAb1 | IgG2a |  | 97 |
| NegativeAb2 | IgG1 | 90 | 98 |

Negative Ab1 and Negative Ab2 indicate antibodies that recognize antigens that are not expressed in human cell lines and unrelated to CDH3.

PPAT-055-03 hybridoma that produces the PPAT-055-03 antibody was deposited at the National Institute of Technology and Evaluation, Patent Microorganisms Depositary (2-5-8, Kazusakamatari, Kisarazushi, Chiba, 292-0818, Japan) under Accession Number: NITE P-988 on Oct. 15, 2010 and was transferred, under Accession Number: NITE BP-988, to the international deposit under the Budapest Treaty as of Sep. 7, 2011.

PPAT-055-09 and PPAT-055-24 hybridomas that produce the PPAT-055-09 and PPAT-055-24 antibodies were deposited at the National Institute of Technology and Evaluation, Patent Microorganisms Depositary (2-5-8, Kazusakamatari, Kisarazushi, Chiba, 292-0818, Japan) under Accession Numbers: NITE BP-989 and NITE BP-991, respectively, on Oct. 15, 2010 and were transferred, under Accession Numbers: NITE BP-989 and NITE BP-991, respectively, to the international deposit under the Budapest Treaty as of Sep. 7, 2011.

PPAT-055-15 hybridoma that produces the PPAT-055-15 antibody was deposited internationally at the National Institute of Technology and Evaluation, Patent Microorganisms Depositary (2-5-8, Kazusakamatari, Kisarazushi, Chiba, 292-0818, Japan) under Accession Number: NITE BP-1145 under the Budapest Treaty.

Example 7

Classification of Anti-CDH3 Monoclonal Antibody Based on Epitope

Figure 8:
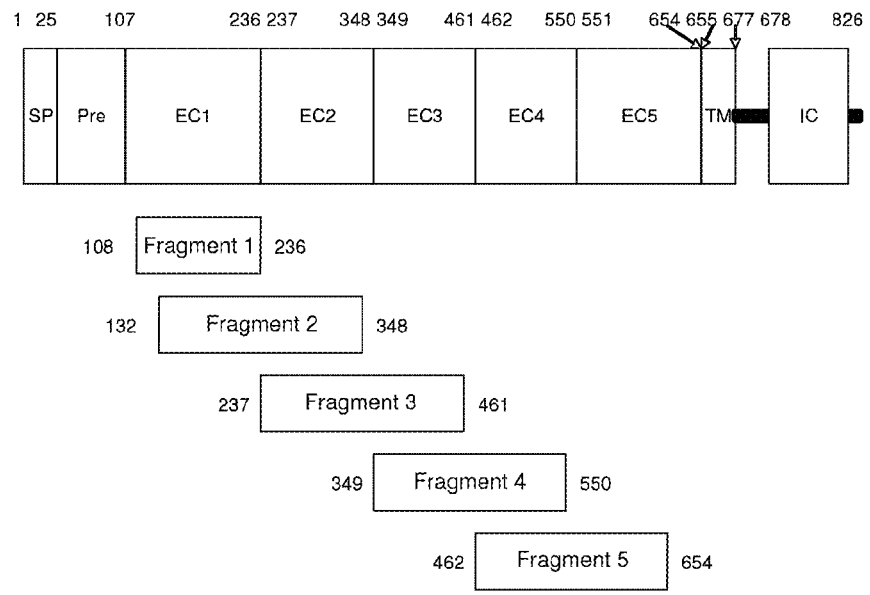
FIG. 8 shows the human CDH3 extracellular domains corresponding to partial protein fragments 1 to 5 of human CDH3.

Epitope-based classification of the obtained anti-human CDH3 antibody was carried out based on the reaction thereof with a fragment expressing a partial sequence of human CDH3 analyzed by Western blotting. In order for sequences to sufficiently overlap with each other between fragments, fragments 1 to 5 expressing a partial sequence of human CDH3 were designed (FIG. 8).

(1) Production of Expression Vector for Fragment Expressing Partial Sequence of Human CDH3

PCR was performed with the use of the full-length human CDH3 cDNA of Example 3 as a template and the sets of primers described below. The reaction was carried out with the use of iProof high-fidelity DNA polymerase (Bio-Rad Laboratories, Inc.) by repeating a cycle of 98° C. for 10 seconds, 60° C. for 10 seconds, and 72° C. for 30 seconds 35 times. A gel fragment containing a band with a size similar to the target size was cleaved via agarose gel electrophoresis, and a partial sequence of human CDH3 cDNA of interest was obtained using a QIA® quick gel extraction kit.

In order to insert the partial sequence of human CDH3 into an *E. coli* expression vector (pCold® TF, Takara Bio Inc.), the partial sequence was treated with two restriction enzymes KplII and XbaI. The thus-obtained fragment was then inserted into pCold TF, which had been treated with the same restriction enzymes KpnI and XbaI, with the use of T4 DNA ligase in accordance with a conventional technique, and expression vectors for the fragments were obtained. PCR was carried out using the sets of primers described below so that each fragment was obtained.

```
Fragment 1 (positions 108 to 236 of
SEQ ID NO: 2)
Forward primer:
                                        (SEQ ID NO: 9)
TATGGAGCTCGGTACCGATTGGGTGGTTGCTCCAATATCTG Reverse primer:
                                       (SEQ ID NO: 10)
AGATTACCTATCTAGACTACTGCATCACAGAAGTACCTGGTAGG Fragment 2 (positions 132 to 348 of
SEQ ID NO: 2)
Forward primer:
                                       (SEQ ID NO: 11)
TATGGAGCTCGGTACCAAGTCTAATAAAGATAGAGACACCAAG Reverse primer:
                                       (SEQ ID NO: 12)
AGATTACCTATCTAGACTACCTCTGCACCTCATGGCCCACTGCATTCTCA Fragment 3 (positions 237 to 461 of
SEQ ID NO: 2)
Forward primer:
                                       (SEQ ID NO: 13)
TATGGAGCTCGGTACCGTGACAGCCACGGATGAGGATGATG Reverse primer:
                                       (SEQ ID NO: 14)
AGATTACCTATCTAGACTAGACACACACAGGCTCCCCAGTG Fragment 4 (positions 349 to 550 of
SEQ ID NO: 2)
Forward primer:
                                       (SEQ ID NO: 15)
TATGGAGCTCGGTACCCTGACGGTCACTGATCTGGACG Reverse primer:
                                       (SEQ ID NO: 16)
AGATTACCTATCTAGACTAGGGCTCAGGGACTGGGCCATGGTCATTG Fragment 5 (positions 462 to 654 of
SEQ ID NO: 2)
Forward primer:
                                       (SEQ ID NO: 17)
TATGGAGCTCGGTACCTACACTGCAGAAGACCCTGACAAGG Reverse primer:
                                       (SEQ ID NO: 18)
AGATTACCTATCTAGACTAACCTCCCTTCCAGGGTCCAGGGCAGGTTTCG
```

(2) Expression of Partial Sequence of Human CDH3

With the use of the expression vector for the CDH3 fragment of (1), *E. coli* Rossetta® 2 cells (Merck) were transformed in accordance with a conventional technique, and the transformed cells were cultured in an LB medium. When the absorbance at 600 nm reached 0.4, the culture product was ice-cooled for 30 minutes, isopropyl-β-thiogalactopyranoside (IPTG) concentration was adjusted to 0.5 mM, and culture was conducted at 20° C. for 18 hours, followed by recovery of the culture product.

Expression of the partial sequence of human CDH3 was inspected by electrophoresis of the *E. coli* culture solution, followed by Western blot analysis using the anti-Penta-His antibody (Qiagen) to detect the presence of a band at a deduced position.

Figure 9:
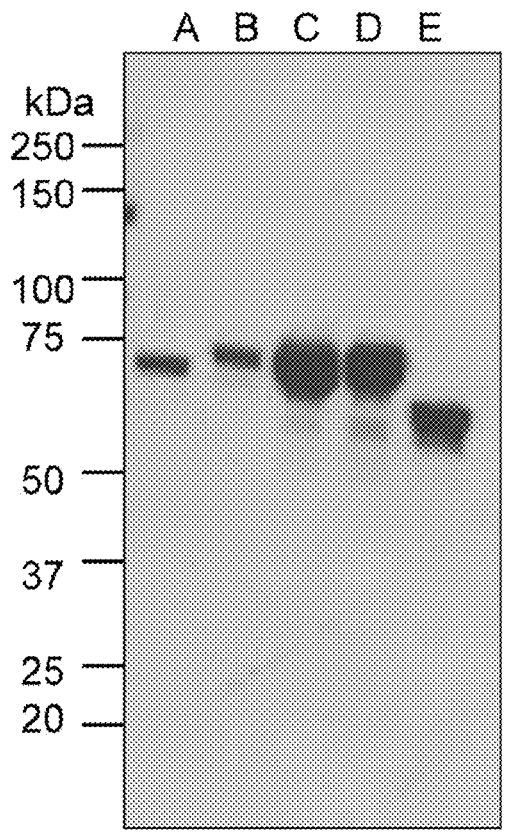
FIG. 9 shows the results of human CDH3 partial protein expression (A: fragment 1; B: fragment 2; C: fragment 3; D: fragment 4; and E: fragment 5).

Specifically, an electrophoresis buffer in an amount equal to one-tenth of the amount of the *E. coli* culture solution was added, the mixture was loaded and electrophoresed on 5% to 20% gradient gel (Bio-Rad Laboratories, Inc.) under reducing conditions, and the resultant was transferred to Immobilon® P (Millipore Corporation). The transfer membrane was washed softly with TBS-T (0.05% Tween® 20, TBS) and then subjected to shaking in TBS containing 40% BSA for 1 hour. Thereafter, anti-CDH3 antibodies diluted with TBS-T containing 10% Block Ace® (Snow Brand Milk Products, Co. Ltd.) were added thereto, and the membrane was subjected to shaking for 1 hour. The membrane was washed with TBS-T, subjected to shaking with the HRP-anti-mouse IgG antibody (GE Healthcare Biosciences Inc.) diluted with TBS-T containing 10% Block Ace for 1 hour, and then washed with TBS-T. Color development was detected using ECL®-Plus (GE Healthcare Biosciences Inc.) and an X-ray film (RX-u, Fuji Film Corporation) in accordance with the instructions given by the manufacturers. FIG. 9 shows the results of detection.

(3) Classification of Antibody Based on Epitope Using Expression Product of Partial CDH3 Sequence

Figure 10:
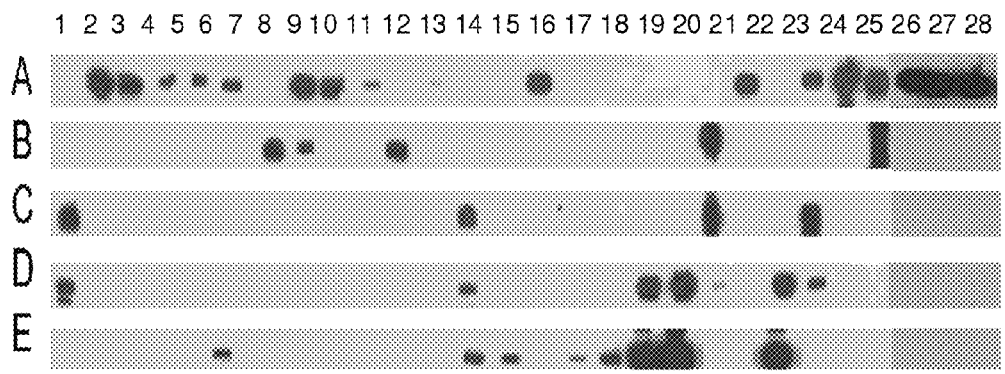
FIG. 10 shows the reactions of human CDH3 partial proteins and various antibodies analyzed by Western blotting (A: fragment 1; B: fragment 2; C: fragment 3; D: fragment 4; and E: fragment 5).

*E. coli* lysates in which the aforementioned partial CDH3 sequences had been expressed were loaded and electrophoresed on 5% to 20% gradient gel (Bio-Rad Laboratories, Inc.) under reducing conditions, and the resultants were transferred to Immobilon P (Millipore Corporation) using a blotting apparatus (Bio-Rad Laboratories, Inc.). The transfer membrane was washed softly with TBS-T (0.05% Tween® 20, TBS) and then subjected to shaking in TBS containing 40% BSA for 1 hour. Thereafter, the membrane was cut into strips of equal width, anti-CDH3 antibodies diluted with TBS-T containing 10% Block Ace were added thereto, and the membrane was subjected to shaking for 1 hour. The membrane was washed with TBS-T, subjected to shaking with the HRP-anti-mouse IgG antibody (GE Healthcare Biosciences Inc.) diluted with TBS-T containing 10% Block Ace for 1 hour, and then washed with TBS-T. Color development was detected using ECL®-Plus (GE Healthcare Biosciences Inc.) and an X-ray film (RX-u, Fuji Film Corporation) in accordance with the instructions given by the manufacturers. FIG. 10 shows the results of detection. Based on the reactivity with the expression product of CDH3 partial sequences, domains recognized by the antibodies were determined.

(4) Determination of Anti-CDH3 Monoclonal Antibody Epitope Using Peptide Array

When determining an epitope using the expression product of partial CDH3 sequences described in (3) above, the PPAT-055-13 antibody that was considered to correspond to the epitope boundary was applied to a peptide array (Replitope; manufactured by JPT Peptide Technologies) and subjected to epitope determination in greater detail. Specifically, regarding a region corresponding to the extracellular region of CDH3 (which corresponds to positions 108-563 of SEQ ID NO: 2), a peptide of 13 residues was designed and synthesized, while each initial residue was shifted by every two amino acid residues from the N-terminus (that is, positions 108-120, 110-122, . . . and 551-563). The thus synthesized peptides were immobilized on a glass slide, and were then blocked by SuperBlock (Thermo Fisher Scientific Inc.). The thus prepared product was reacted with an antibody which is an epitope searching target as a primary antibody. The reaction product was washed three times with TBS-T, and detection was then carried out using an anti-mouse antibody (Thermo Fisher Scientific Inc.) that had been fluorescently labeled with DyLight 649. An antibody that had not been allowed to react with the antibody which is an epitope searching target was used as a negative control in the assays. The results of assays are shown in FIG. 11. Strong signals were observed in regions corresponding to positions 446-472 and 490-504 of the amino acid sequence of CDH3 shown in SEQ ID NO: 2, and these were assumed to be epitopes of the present antibody.

The correlation regarding the regions in the CDH3 sequence recognized by the antibodies deduced based on the experiment above is shown in Table 2 together with the results of internalization test shown in Table 1.

TABLE 2

| Antibody No. | Subtype | Cell viability (%, Test A) | Cell viability (%, Test B) | Recognition domain |
|---|---|---|---|---|
| PPAT-055-01 | IgG1 | 92 | 85 | EC3 |
| PPAT-055-02 | IgG2a | 31 | 42 | EC1 |
| PPAT-055-03 | IgG1 | 34 | 50 | EC1 |
| PPAT-055-05 | IgG1 |  | 69 | EC1 |
| PPAT-055-07 | IgG2a |  | 45 | EC1 |
| PPAT-055-08 | IgG2a | 43 | 40 | EC1 |
| PPAT-055-09 | IgG1 | 26 | 57 | EC1 |
| PPAT-055-10 | IgG1 |  | 61 | EC1 |
| PPAT-055-11 | IgG1 |  | 59 | EC1 |
| PPAT-055-12 | IgG2a | 47 | 58 | EC1 |
| PPAT-055-13 | IgG1 | 99 | 95 | EC3 |
| PPAT-055-14 | IgG1 |  | 87 | EC4 |
| PPAT-055-15 | IgG1 | 23 |  | EC1 |
| PPAT-055-16 | IgG1 | 88 | 89 | EC5 |
| PPAT-055-17 | IgG1 | 93 | 87 | EC5 |
| PPAT-055-18 | IgG1 |  | 65 | EC4 |
| PPAT-055-19 | IgG2b | 85 | 79 | EC4 |
| PPAT-055-20 | IgG2a |  | 78 | EC2 |
| PPAT-055-21 | IgG2a |  | 57 | EC1 |
| PPAT-055-24 | IgG2a |  | 44 | EC1 |
| PPAT-055-25 | IgG1 |  | 54 | EC1 |

* PPAT-055-13 was deduced to recognize the boundary between EC3 and EC4.

The relationship between the recognition domains in the table and the amino acid position shown in SEQ ID NO: 2 are as follows.
EC1: positions 108 to 236
EC2: positions 237 to 348
EC3: positions 349 to 461
EC4: positions 462 to 550
EC5: positions 551 to 654

Based on the results of determination of the domains to be recognized by the antibodies, the relationship between the recognition domain and the internalization capacity was examined. As a result, antibodies having a high internalization capacity were found to be concentrated in the EC1 domain of human CDH3.

Example 8

Purification of RNA from Hybridomas

Cytoplasmic RNAs were isolated from the PPAT-055-09 hybridoma (Accession Number NITE BP-989) and the PPAT-055-24 hybridoma (Accession Number NITE BP-991) in accordance with the method described by Gough (Rapid and quantitative preparation of cytoplasmic RNA from small numbers of cells, Analytical Biochemisty, 173, pp. 93-95, 1988), although a different TNE buffer (25 mM Tris-HCl, pH 7.5, 1% NP-40, 150 mM NaCl, 1 mM EDTA, pH 8.0) was used instead of a lysis buffer described therein. Specifically, $5 \times 10^6$ hybridoma cells were suspended in 0.2 ml of TNE buffer to lyse the cytoplasmic membrane, and cell nuclei were then removed via centrifugation. An extraction buffer (0.2 ml, 10 mM Tris-HCl, pH 7.5, 0.35 M NaCl, 1%(w/v) SDS, 10 mM EDTA, pH 8.0, 7 M urea) was added to about 0.2 ml of the resulting cytoplasmic supernatant. The mixture was subjected to phenol- and chloroform-extraction, and a glycogen carrier (Cat No. 901393, Roche Diagnostics K.K.) was added to the resulting RNA solution, followed by ethanol precipitation. Subsequently, the RNA precipitate was lysed with the addition of 10 to 50 µl of sterile distilled water to a cytoplasmic RNA concentration of 0.5 to 2 µg/µl.

Example 9

Production of cDNA Library from RNA Prepared from Hybridoma

In order to synthesize a single chain cDNA, 20 µl of a reaction mixture containing 0.5 to 3 µg of the above-prepared cytoplasmic RNA, 50 mM Tris-HCl (pH 8.3, room temperature), 75 mM KCl, 3 mM $MgCl_2$, 10 mM DTT, 100 ng of a random primer, 0.5 mM dNTP, and 200 units of Superscript II (reverse transcriptase, Invitrogen) was prepared, and the mixture was incubated at 42° C. for 50 minutes. The thus-synthesized cDNA library was directly employed as a template of polymerase chain reaction (PCR).

Example 10

Amplification of Gene Encoding Variable Region of Anti-Human CDH3 Antibody by PCR All the primers employed in the experiments were synthesized by Hokkaido System Science Co., Ltd.
A. Primers for Use in PCR Amplification of Gene Encoding Mouse Light Chain Variable Region
The following two primer sets were employed: (1) a DNA primer having, at the 5' end, a homology to the FR1 part and 4-set primers having, at the 3' end, a homology to a J-chain gene in the mouse L-chain, and (2) 7-set primers having, at the 5' end, a homology to the L-chain signal part and an antisense primer having, at the 3' end, a homology to the KC part (KVL antisense primer). Polymerase chain reaction was performed with the use of the two primer sets, whereby mouse immunoglobulin L-chain variable region DNA was isolated from the cDNA. The primer sequences are as follows.

(1) 4-Set Sense Primers for Cloning of Mouse L-Chain Variable Region

According to "Phage Display-A Laboratory Manual-, Barbas Burton Scott Silverman," PROTOCOL 9.5, 17 types of sense primers and 3 types of reverse primers were synthesized by Hokkaido System Science Co., Ltd.

VK Sense (FR1 Part)

A mixture of the following 17 primers was employed as a VK sense (FR1 part) primer. In nucleotide sequences, W indicates A or T, R indicates A or G, M indicates A or C, K indicates T or Y indicates T or C, S indicates G or C, H indicates A, C, or T, B indicates G, C, or T, V indicates A, G, or C, D indicates A, G, or T, and N indicates A, G, C, or T.

```
SEQ ID NO: 19:
5'-GAYATCCAGCTGACTCAGCC-3'      (degeneracy: 2)

SEQ ID NO: 20:
5'-GAYATTGTTCTCWCCCAGTC-3'      (degeneracy: 4)

SEQ ID NO: 21:
5'-GAYATTGTGMTMACTCAGTC-3'      (degeneracy: 8)

SEQ ID NO: 22:
5'-GAYATTGTGYTRACACAGTC-3'      (degeneracy: 8)

SEQ ID NO: 23:
5'-GAYATTGTRATGACMCAGTC-3'      (degeneracy: 8)

SEQ ID NO: 24:
5'-GAYATTMAGATRAMCCAGTC-3'      (degeneracy: 16)

SEQ ID NO: 25:
5'-GAYATTCAGATGAYDCAGTC-3'      (degeneracy: 12)

SEQ ID NO: 26:
5'-GAYATYCAGATGACACAGAC-3'      (degeneracy: 4)

SEQ ID NO: 27:
5'-GAYATTGTTCTCAWCCAGTC-3'      (degeneracy: 4)

SEQ ID NO: 28:
5'-GAYATTGWGCTSACCCAATC-3'      (degeneracy: 8)

SEQ ID NO: 29:
5'-GAYATTSTRATGACCCARTC-3'      (degeneracy: 16)

SEQ ID NO: 30:
5'-GAYRTTKTGATGACCCARAC-3'      (degeneracy: 16)

SEQ ID NO: 31:
5'-GAYATTGTGATGACBCAGKC-3'      (degeneracy: 12)

SEQ ID NO: 32:
5'-GAYATTGTGATAACYCAGGA-3'      (degeneracy: 4)

SEQ ID NO: 33:
5'-GAYATTGTGATGACCCAGWT-3'      (degeneracy: 4)

SEQ ID NO: 34:
5'-GAYATTGTGATGACACAACC-3'      (degeneracy: 2)

SEQ ID NO: 35:
5'-GAYATTTTGCTGACTCAGTC-3'      (degeneracy: 2)
```

J Antisense (4-Set Primers)

```
J1/J2 antisense primer (1)
SEQ ID NO: 36:
5'-GGSACCAARCTGGAAATMAAA-3'     (degeneracy: 8)

J4 antisense primer (2)
SEQ ID NO: 37:
5'-GGGACAAAGTTGGAAATAAAA-3'

J5 antisense primer (3)
SEQ ID NO: 38:
5'-GGGACCAAGCTGGAGCTGAAA-3'
```

J1/J2, J4, 55 Antisense Primer Mixture (4)

(2) 7-Set Primers for Cloning of Mouse L-Chain Variable Region

VK Sense (Signal Peptide Part)

The primers were obtained by nucleotide sequence modification of a mouse Ig-primer set (Novagen; Merck, Cat. No. 69831-3) and restriction enzyme sites were thus removed therefrom.

A Set Sense Primer

```
SEQ ID NO: 39:
5'-ATGRAGWCACAKWCYCAGGTCTTT-3'
```

B Set Sense Primer

```
SEQ ID NO: 40:
5'-ATGGAGACAGACACACTCCTGCTAT-3'
```

C Set Sense Primer

```
SEQ ID NO: 41:
5'-ATGGAGWCAGACACACTSCTGYTATGGGT-3'
```

D Set Sense Primer (A Mixture of the Following 2 Primers)

```
SEQ ID NO: 42:
5'-ATGAGGRCCCCTGCTCAGWTTYTTGGIWTCTT-3'

SEQ ID NO: 43:
5'-ATGGGCWTCAAGATGRAGTCACAKWYYCWGG-3'
```

E Set Sense Primer (A Mixture of the Following 3 Primers)

```
SEQ ID NO: 44:
5'-ATGAGTGTGCYCACTCAGGTCCTGGSGTT-3'

SEQ ID NO: 45:
5'-ATGTGGGGAYCGKTTTYAMMCTTTTCAATTG-3'

SEQ ID NO: 46:
5'-ATGGAAGCCCCAGCTCAGCTTCTCTTCC-3'
```

F Set Sense Primer (A Mixture of the Following 4 Primers)

```
SEQ ID NO: 47:
5'-ATGAGIMMKTCIMTTCAITTCYTGGG-3'

SEQ ID NO: 48:
5'-ATGAKGTHCYCIGCTCAGYTYCTIRG-3'

SEQ ID NO: 49:
5'-ATGGTRTCCWCASCTCAGTTCCTTG-3'

SEQ ID NO: 50:
5'-ATGTATATATGTTTGTTGTCTATTTCT-3'
```

G Set Sense Primer (A Mixture of the Following 4 Primers)

```
SEQ ID NO: 51:
5'-ATGAAGTTGCCTGTTAGGCTGTTGGTGCT-3'

SEQ ID NO: 52:
5'-ATGGATTTWCARGTGCAGATTWTCAGCTT-3'
```

-continued

SEQ ID NO: 53:
5'-ATGGTYCTYATVTCCTTGCTGTTCTGG-3'

SEQ ID NO: 54:
5'-ATGGTYCTYATVTTRCTGCTGCTATGG-3'

K VL Antisense Primer

SEQ ID NO: 55:
5'-ACTGGATGGTGGGAAGATGGA-3'

B. Primers for Use in PCR Amplification of Gene Encoding Mouse H-Chain V-Region

The following two primer sets were employed: 4-set primers having, at the 5' end, a homology to the mouse H-chain signal part and a primer having, at the 3' end, a homology to the KC part; and 1 set of primers each having, at the 5' end, a homology to the FR1 part and 2-types primer having, at the 3' end, a homology to the mouse H-chain constant region (IGHC). Polymerase chain reaction was performed with the use of the two primer sets, whereby DNA of the mouse immunoglobulin H-chain variable region was isolated from the cDNA. The primer sequences are as follows (3) Primers for Cloning of Mouse H-Chain Variable Region VH Sense (Signal Part: 4-Set Primers)

These primers were synthesized according to Current Protocols in Immunology (John Wiley and Sons, Inc.), Unit 2.12 Cloning, Expression, and Modification of Antibody V Regions (Table 2.12.2).

SEQ ID NO: 56:
5'-ATGGRATGSAGCTGKGTMATSCTCTT-3'    (degeneracy: 32)

SEQ ID NO: 57:
5'-ATGRACTTCGGGYTGAGCTKGGTTTT-3'    (degeneracy: 8)

SEQ ID NO: 58:
5'-ATGGCTGTCTTGGGGCTGCTCTTCT-3'

SEQ ID NO: 59:
5'-ATGGRCAGRCTTACWTYY-3'    (degeneracy: 32)

(4) Primers for Cloning of Mouse H-Chain Variable Region

VH Sense (FR1 Part)

These primers were designed by nucleotide sequence modification of sense primers disclosed in a document (Tan et al, "Superhumanized" Antibodies: Reduction of Immunoogenic Potential by Complementarity-Determining Region Grafting with Human Germline Sequences: Application to an Anti-CD281, Journal of Immunology 169, 2002, pp. 1119-1125).

SEQ ID NO: 60:
5'-SAGGTSMARCTKSAGSAGTCWGG-3'    (degeneracy: 256)

VH Antisense (Antisense Primer Common to 3 and 4)

The primer was designed through degeneration of the nucleotide sequence, so that the primer would be annealed with all the isoforms of mouse IgG.

SEQ ID NO: 61:
5'-CASCCCCATCDGTCTATCC-3'    (degeneracy: 6)

Example 11

Production of Transient Expression Vector for Chimera Anti-Human-CDH3 Immunoglobulin Production of Expression Plasmid:

Through PCR using the DNA Engine (Peltier Thermal Cycler, Bio-Rad Laboratories, Inc.), each variable region of the L-chain and the H-chain of an anti-CDH3 mouse monoclonal antibody was amplified with the use of the primers described in Example 10. Each of the thus-amplified DNA fragments was incorporated into a sub-cloning vector pGEM (Promega). The nucleotide sequence of the DNA fragment was determined with the use of T7 and SP6 universal primers of the vector.

The nucleotide sequences of L-chain and H-chain variable regions of the chimera anti-human CDH3 antibody thus obtained were searched for by IMGT/V-QUEST Search page (http://www.imgt.org/IMGT_vquest/vquest?livret=0&Option=mouseIg), whereby completion of cloning of the antibody genes was confirmed.

Subsequently, a gene encoding the human Cκ region was designed to be linked to a chimeric L-chain expression vector, and a gene encoding the human Cg1 region was designed to be linked to a chimeric H chain expression vector to construct genes encoding V regions of the L-chain and the H-chain of the cloned anti-CDH3 antibody. The thus-designed L-chain and H-chain chimeric antibody genes were synthesized in full length by GenScript Inc. At that time, frequency of codon usage was optimized so as to achieve efficient gene expression in CHO-producing cells (according to a method disclosed in Kim et al., Codon optimization for high-level expression of human erythropoietin (EPO) in mammalian cells, Gene, 199, 1997, pp. 293-301). In the case of L-chain, specifically, an essential DNA sequence for the effective translation (Kozak, M., J., At least six nucleotides preceding the AUG initiator codon enhance translation in mammalian cells, J. Mol. Biol. 196, pp. 947-950, 1987), a signal peptide of mouse IGKV (a x-chain variable region), the V region of the L-chain of the anti-CDH3 antibody, and the human KC region (i.e., a k chain constant region) were juxtaposed in this order, and restriction enzyme sites were added to both ends (NheI on the 5' side and EcoRI on the 3' side). The chimera H-chain was prepared in the same manner. Each of the artificially synthesized genes was cleaved with NheI and EcoRI, and the cleaved fragment was incorporated into an expression vector pCAGGS between the NheI site and the EcoRI site, to thereby produce an anti-human CDH3 chimeric antibody L-chain expression vector pCAGGS-IGK and an H-chain expression vector pCAGGS-IGH.

Example 12

Production of Stable Expression Vector for Anti-Human CDH3 Chimeric Antibody

In order to realize high-level expression of a genetically engineered antibody gene in CHO cells, an expression vector in which a dihydrofolate reductase (dhfr) gene linked to a CMV promoter sequence and having poly A signal was inserted, was puced.

In order to produce a chimeric antibody-stably expressing/producing cell line, a pCAGGS expression vector into which a dhfr gene was inserted, was produced. Specifically, a dhfr gene having a CMV promoter and poly A signal was inserted into pCAGGS-IGH and pCAGGS-IGK, which are transient expression vectors. A CMV promoter, a mouse dhfr gene having the Kozak sequence, and SV40 poly A signal were amplified via PCR. These genes in mixture form were linked together via PCR, and an HindIII site was added to both ends of the linked product, to thereby obtain a gene fragment of HindIII-CMV promoter-Kozak-dhfr-poly A-HindIII. The fragment was inserted into the HindIII site of pCAGGS-IGH or pCAGGS-IGK, to thereby obtain pCAGGS-IGH-CMVp-dhfr-A and pCAGGS-IGK-CMVp-dhfr-A. These expression vectors enable expression of chimeric antibody with a CAG promoter, and expression of a dhfr gene with a CMV promoter, whereby a chimeric antibody can be effectively produced through gene amplification.

Example 13

Establishment of CHO Cell Line which Produces Anti-Human CDH3 Chimeric Antibody CHO dhfr(−) cells (G. Urlaub et al., Isolation of Chinese hamster cell mutants deficient in dihydrofolate reductase activity, Proc. Natl. Acad. Sci. U.S.A., 77, pp. 4216-4220, 1980) were simultaneously transformed with the use of two plasmids (linear plasmids obtained by cleaving circular plasmids with PvuI in an ampicillin-resistant gene); i.e., a pCAGGS-IGK-CMV-dhfr-A vector for expression of chimera anti-CDH3 L chain and a pCAGGS-IGH-CMV-dhfr-A vector for expression of chimera anti-CDH3 H chain. Electroporation was performed by means of Amaxa (Lonza). A DNA (0.002 mg/sample; in the case of L-chain plasmid or H-chain plasmid) was added to a 0.1 ml of Amaxa electroporation CHO buffer containing 3×10e3 cells, and a pulse was applied.

The cells which had been subjected to electroporation were added to an Iscove's Modified Dulbecco medium (IMDM) free of HT (H: hypoxanthine; T: thymidine) containing 10% dialyzed FBS. Three days after transfection, the medium was exchanged with an IMDM medium free of 10% dialyzed FBS, 2 mM L-glutamine and HT, and neo+ transformed cells were selected with the use of 1 mg/ml G418, to thereby obtain clones of a chimeric antibody-producing positive cell line. Subsequently, gene amplification was performed with the use of the clones selected with the use of G418. Two-round amplification was performed in 0.25 mM methotrexate (MTX) and 1 mM (MTX), and cell lines which can produce a chimera anti-human CDH3 antibody (about 50 to 100 mg/l) were established.

Example 14

Quantification of Chimeric Antibody via Enzyme Immunoassay (ELISA)

The culture supernatant of the transfected CHO cells was analyzed via ELISA to confirm the production of the chimeric antibody. In order to detect a chimeric antibody, a plate was coated with goat anti-human IgG (H+L) (preabsorbed with mouse, rabbit, bovine, and mouse IgG) (AQI, Cat. A-11OUD; COSMO BIO Co., Ltd.). After blocking, the culture supernatant obtained from CHO cells producing anti-CDH3 chimeric antibody was subjected to serial dilution, and was added to the wells. After the plate was subjected to incubation and washing, goat anti-human IgG (H+L) (preabsorbed with mouse, rabbit, bovine, and mouse IgG)-HRP (AQI, Cat. A-110 PD; COSMO BIO Co., Ltd.) was added. Following incubation and washing, a substrate buffer was added. Incubation was further carried out, the reaction was terminated, and the absorbance at 450 nm was then assayed. Purified human IgG was used as the standard.

Example 15

Evaluation of Internalization Capacity of Chimeric Antibody

The internalization capacity of the chimeric antibody prepared was assayed in the same manner as in Example 6, except that HumZAP (Advanced Targeting Systems, Inc.) was used as a saporin-labeled antibody in order to deal with a chimeric antibody. As a result, the chimeric antibody was found to maintain the internalization capacity observed in the parental antibody. Table 3 shows the results of the internalization test of the chimeric antibody in combination with the results of the parental antibody shown in Table 1.

TABLE 3

| Parental antibody No. | Subtype | Cell viability of parental antibody (%, Test A) | Cell viability of parental antibody (%, Test B) | Recognition domain | Chimeric antibody No. | Cell viability of chimeric antibody (%) |
|---|---|---|---|---|---|---|
| PPAT-055-15 | IgG1 | 23 | | EC1 | | |
| PPAT-055-08 | IgG2a | 43 | 40 | EC1 | | |
| PPAT-055-02 | IgG2a | 31 | 42 | EC1 | | |
| PPAT-055-24 | IgG2a | | 44 | EC1 | PPAT-055-24C | 41 |
| PPAT-055-07 | IgG2a | | 45 | EC1 | | |
| PPAT-055-03 | IgG1 | 34 | 50 | EC1 | | |
| PPAT-055-25 | IgG1 | | 54 | EC1 | | |
| PPAT-055-09 | IgG1 | 26 | 57 | EC1 | PPAT-055-09C | 44 |
| PPAT-055-21 | IgG2a | | 57 | EC1 | | |
| PPAT-055-12 | IgG2a | 47 | 58 | EC1 | | |
| PPAT-055-11 | IgG1 | | 59 | EC1 | | |
| PPAT-055-10 | IgG1 | | 61 | EC1 | | |
| PPAT-055-18 | IgG1 | | 65 | EC4 | | |
| PPAT-055-05 | IgG1 | | 69 | EC1 | | |
| PPAT-055-20 | IgG2a | | 78 | EC2 | | |
| PPAT-055-19 | IgG2b | 85 | 79 | EC4 | | |
| PPAT-055-01 | IgG1 | 92 | 85 | EC3 | | |
| PPAT-055-14 | IgG1 | | 87 | EC4 | | |
| PPAT-055-17 | IgG1 | 93 | 87 | EC5 | PPAT-055-17C | 91 |
| PPAT-055-16 | IgG1 | 88 | 89 | EC5 | | |
| PPAT-055-13 | IgG1 | 99 | 95 | EC3 | | |

TABLE 3-continued

| Parental antibody No. | Subtype | Cell viability of parental antibody (%, Test A) | Cell viability of parental antibody (%, Test B) | Recognition domain | Chimeric antibody No. | Cell viability of chimeric antibody (%) |
|---|---|---|---|---|---|---|
| NegativeAb1 | IgG2a | | 97 | | | |
| NegativeAb2 | IgG1 | 90 | 98 | | | |

\* PPAT-055-13 was deduced to recognize the boundary between EC3 and EC4.

PPAT-055-9C and PPAT-055-24C cell lines that produce the PPAT-055-9C and PPAT-055-24C chimeric antibodies were internationally deposited at the National Institute of Technology and Evaluation, Patent Microorganisms Depositary (2-5-8, Kazusakamatari, Kisarazushi, Chiba, 292-0818, Japan) under Accession Numbers: NITE BP-1147 and NITE BP-1148, respectively, on Sep. 27, 2011 under the Budapest Treaty.

Example 16

Drug Synthesis

Figure 12:
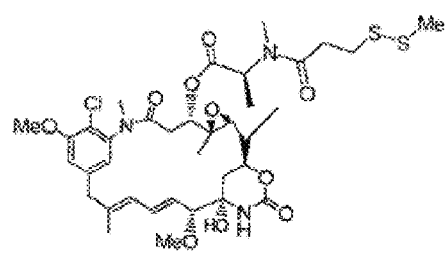
FIG. 12 shows the structure of DM1SMe.

DM1SMe was prepared in the manner described in U.S. Pat. Nos. 5,208,020 and 6,333,410B1 (FIG. 12).

Example 17

Preparation of Drug-Conjugated Antibody (1) Reduction Treatment of Drug to be Conjugated A solution of 0.78 mg of DM1SMe dissolved in 300 μl of ethanol, 180 μl of 50 mM potassium phosphate buffer (pH 7.5), and 20 μl of TCEP solution (Bond Breaker, Thermo Fisher Scientific Inc.) were mixed, and the resulting mixture was subjected to the reaction under the nitrogen atmosphere at room temperature for at least 30 minutes with agitation to reduce the drugs.

The reduced drugs were purified via HPLC, the solvent was removed therefrom by distillation, and the resultant was dissolved in dimethyl acetamide to a drug concentration of 10 mg/ml.

(2) Preparation of Antibody Conjugated to Maleimide

A 30-fold molar excess of sulfo-SMCC (Thermo Fisher Scientific Inc.) was added to 1 mg/ml anti-human CDH3 chimeric antibody, and the reaction was allowed to proceed at 30° C. for 1 hour.

In order to remove excess crosslinking agents, the reaction product was subjected to desalting with the use of the Zeba Spin desalting columns (Thermo Fisher Scientific Inc.) equilibrated with 50 mM potassium phosphate, 50 mM NaCl, and 2 mM EDTA (pH 6.5).

(3) Modification of Antibody with Drug

The anti-CDH3 chimeric antibody conjugated to maleimide (1 mg/ml) and a reduced drug in an amount equal to 1.7 times greater than that of the number of the conjugated maleimide groups were subjected to the reaction in 50 mM potassium phosphate, 50 mM NaCl, and 2 mM EDTA (pH 6.5) at room temperature overnight. Gel filtration was carried out via HPLC in order to remove excess drugs.

Example 18

Quantification of Antibody-Drug Conjugation

The number of drugs conjugated to an antibody was determined by assaying the absorbance at 252 nm and 280 nm with the use of the absorption constants: $\epsilon Ab_{280}=223,000$ $M^{-1}$ $cm^{-1}$, $\epsilon Ab_{252}=82,510$ $M^{-1}$ $cm^{-1}$, $\epsilon DM1_{280}=5,180$ $M^{-1}$ $cm^{-1}$, and $\epsilon DM1_{252}=26,160$ $M^{-1}$ $cm^{-1}$, described in a non-patent document (Widdison, W. C., Wilhelm, S. D., Cavanagh, E. E., et al., 2006, Semisynthetic maytansine analogues for the targeted treatment of cancer, J. Med. Chem., 49, 4392-4408). As a result, it was deduced that about 3 or 4 drugs were introduced per antibody molecule. The results of assays are shown in Table 4.

TABLE 4

| Chimeric antibody No. | A280 | A252 | Number of drugs conjugated to an antibody molecule |
|---|---|---|---|
| PPAT-055-09C | 1.36 | 1.00 | 3.63 |
| PPAT-055-24C | 1.31 | 0.91 | 3.20 |

Example 19

In Vitro Test

Cytotoxicity and specificity of drug-conjugated antibodies were evaluated using a cell proliferation counting reagent involving the use of a WST-8 coloring substrate (Cell Counting Kit-8, DOJINDO LABORATORIES, Inc.).

Figure 13:
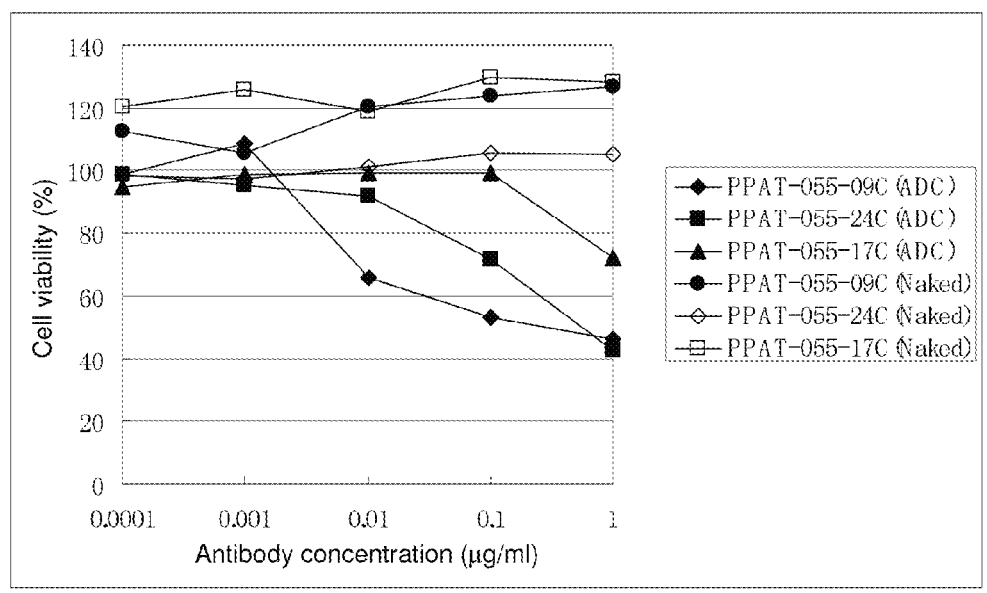
FIG. 13 shows the results of the cytotoxicity test of the anti-human CDH3 chimeric antibody-drug conjugate in vitro (ADC: a clone of the anti-human CDH3 chimeric antibody to which a drug has been linked; Naked: the non-conjugated anti-human CDH3 chimeric antibody).

Specifically, arbitrary amounts of the HCC1954 human breast cancer cells (ATCC CRL-2338), which has been confirmed to exhibit high-level human CDH3 expression, and an antibody-drug conjugate (ADC) or a non-conjugated antibody (Naked) were incubated together at 37° C. in the presence of 5% $CO_2$ for 3 days. Thereafter, a cell proliferation reagent was added, the product was allowed to stand, and the absorbance was assayed at A450/A620. The absorbance assayed in the well to which cancer cells had been added but no antibodies had been added was designated as 100%, and the value relative thereto was expressed as cell viability (FIG. 13).

Example 20

In Vivo Test

The cytoreductive effects of antibody-drug conjugates in vivo were examined using xenograft models to which the HCC1954 human breast cancer cells had been transplanted. Anti-asialo GM1 antibodies (WAKO 014-09801) were dissolved in 1 ml of Otsuka Distilled Water, 4 ml of Otsuka Normal Saline was added thereto to bring the total amount of the solution to 5 ml, and the resulting solution was administered intraperitoneally in an amount of 100 μl per mouse. The HCC1954 cells were cultured in 10% FBS-containing RPMI 1640 medium, and the resultant was transplanted hypodermically to SCID mice (female, CLEA Japan, Inc.) at the right lateral abdominal region to a cell density of $5 \times 10^6$ cells/mouse.

Figure 14:
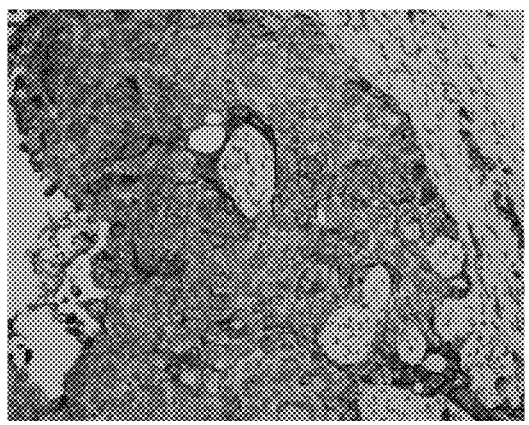
FIG. 14 shows the results of the immunohistostaining analysis of human CDH3 expressed in a tumor mass formed via transplantation of the HCC1954 cell line into a mouse.

Prior to the test, CDH3 expression in the transplanted HCC1954 tumor mass was examined via immunohistochemical (IHC) staining in the same manner as in Example 5. The results are shown in FIG. 14.

The in vivo test was carried out using the groups each consisting of 5 mice, and the drug was administered in an amount of 15 mg/kg through the caudal vein. Administration was initiated when the average tumor size reached 100 to 150 mm$^3$, and the same amount of the drugs was administered 1 week later. That is, drug administration was carried out two times in total.

Figure 15:
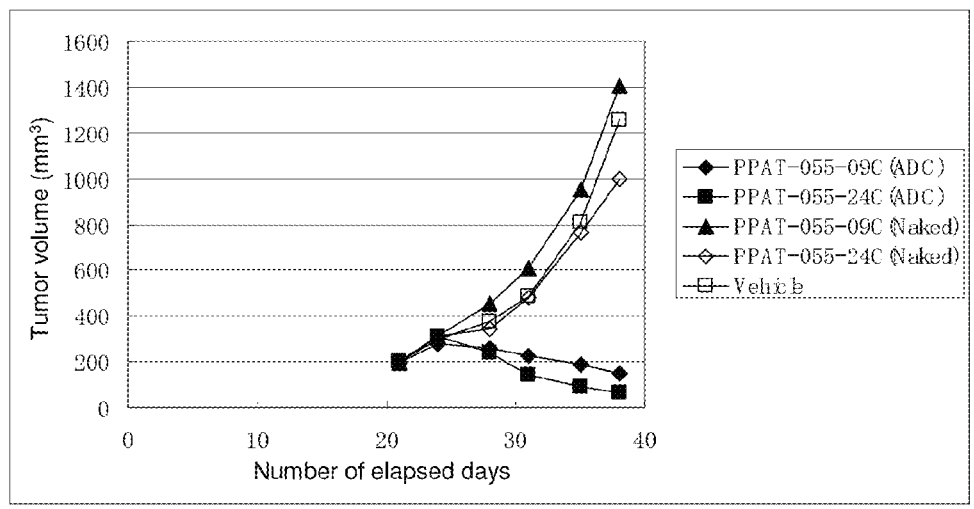
FIG. 15 shows the results of the cytotoxicity test of the human CDH3 chimeric antibody-drug conjugate in vivo (a clone of the anti-human CDH3 chimeric antibody to which a drug has been linked; Naked: the non-conjugated anti-human CDH3 chimeric antibody; Vehicle: antibody lysate).

Changes in tumor sizes are shown in FIG. 15.

The invention claimed is:

1. An anti-cadherin monoclonal antibody which recognizes an extracellular cadherin domain 1 (EC1) of cadherin and exhibits a high internalization capacity, wherein the cadherin is P-cadherin.

2. The antibody according to claim 1, which is produced by an antibody-producing cell obtained from an immunized animal into which P-cadherin or a P-cadherin-expressing cell has been administered as an immunogen.

3. The antibody according to claim 2, wherein the P-cadherin is a full-length cadherin, a soluble P-cadherin obtained by expression of only the extracellular domain, or a fragment thereof that comprises EC1.

4. The antibody according to claim 1, wherein the monoclonal antibody is a chimeric antibody, humanized antibody, or human antibody.

5. A monoclonal antibody which is produced by a cell deposited under Accession Number NITE BP-988, NITE BP-1145, NITE BP-1147, or NITE BP-1148.

6. A cell line which produces the antibody of claim 1.

7. A cell line which is deposited under Accession Number NITE BP-988, NITE BP-1145, NITE BP-1147, or NITE BP-1148.

8. A cytotoxic agent which comprises the antibody of claim 1.

9. The cytotoxic agent according to claim 8, wherein a cytotoxic substance is conjugated to the antibody.

10. The cytotoxic agent according to claim 9, wherein the cytotoxic substance is a drug, toxin, or radioactive substance.

11. The cytotoxic agent according to claim 10, wherein the cytotoxic substance is a drug which is selected from maytansinoid, or auristatin.

12. The cytotoxic agent according to claim 11, wherein the cytotoxic substance is a maytansinoid derivative selected from DM1, DM3 or DM4 or an auristatin derivative selected from MMAE or MMAF.

13. The cytotoxic agent according to claim 9, wherein the antibody is conjugated to a cytotoxic substance via a linker.

14. The cytotoxic agent according to claim 13, wherein the linker is a bifunctional cross-linking agent.

15. The cytotoxic agent according to claim 13, wherein the linker is selected from the group consisting of: sulfosuccinimidyl-4-(N-maleimidomethyl)cyclohexane-1-carboxylate (Sulfo-SMCC), N-succinimidyl-4-(maleimidomethyl)cyclohexanecarboxylate (SMCC), N-succinimidyl-4-(N-maleimidomethyl)-cyclohexane-1-carboxy-(6-amidocaproate) (LC-SMCC), rc-maleimidoundecanoic acid N-succinimidyl ester (KMUA), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl-6-(β-maleimidopropionamido)hexanoate (SMPH), N-succinimidyl-4-(p-maleimidophenyl)-butyrate (SMPB), N-(p-maleimidophenyl)isocyanate (PMPI), 6-maleimidocaproyl (MC), maleimidopropanoyl (MP), p-aminobenzyloxycarbonyl (PAB), N-succinimidyl-4-(2-pyridylthio)pentanoate (SPP), N-succinimidyl(4-iodoacetyl)aminobenzoate (SIAB), valine-citrulline (val-cit), and alanine-phenylalanine (ala-phe).

16. The cytotoxic agent according to claim 14, wherein 1 to 10 DM1 molecules are conjugated to a single antibody molecule via a linker.

17. A pharmaceutical composition which comprises, as an active ingredient, the cytotoxic agent according to claim 8.

18. A therapeutic agent for treating a highly expressed human CDH3 tumor, which comprises, as an active ingredient, the cytotoxic agent of claim 8.

19. The antibody according to claim 5, wherein the monoclonal antibody is a chimeric antibody, humanized antibody, or human antibody.

20. The antibody according to claim 1, wherein the antibody is obtained via administration of EC1 as an antigen to a mammalian animal.

* * * * *